US009445903B2

(12) United States Patent
Meridew et al.

(10) Patent No.: US 9,445,903 B2
(45) Date of Patent: Sep. 20, 2016

(54) MULTI-BEARING ACETABULAR PROSTHESIS

(75) Inventors: Jason D. Meridew, Warsaw, IN (US); Troy W. Hershberger, Winona Lake, IN (US)

(73) Assignee: Biomet Manufacturing, LLC, Warsaw, IN (US)

( * ) Notice: Subject to any disclaimer, the term of this patent is extended or adjusted under 35 U.S.C. 154(b) by 476 days.

(21) Appl. No.: 13/367,408

(22) Filed: Feb. 7, 2012

(65) Prior Publication Data

US 2012/0143343 A1 Jun. 7, 2012

Related U.S. Application Data

(63) Continuation of application No. 12/624,142, filed on Nov. 23, 2009, now Pat. No. 8,123,815.

(60) Provisional application No. 61/117,249, filed on Nov. 24, 2008.

(51) Int. Cl.

| | |
|---|---|
| ***A61F 2/32*** | (2006.01) |
| ***A61F 2/34*** | (2006.01) |
| *A61F 2/30* | (2006.01) |

(52) U.S. Cl.

CPC ........ *A61F 2/34* (2013.01); *A61F 2002/30332* (2013.01); *A61F 2002/30604* (2013.01); *A61F 2002/30607* (2013.01); *A61F 2002/3403* (2013.01); *A61F 2002/3411* (2013.01); *A61F 2002/3414* (2013.01); *A61F 2002/3451* (2013.01); *A61F 2220/0033* (2013.01); *A61F 2250/0062* (2013.01)

(58) Field of Classification Search

CPC ....................... A61F 2/32; A61F 2/34; A61F 2002/300016; A61F 2002/3409

USPC .......... 623/22.19, 22.28, 22.29, 22.34–22.37

See application file for complete search history.

(56) References Cited

U.S. PATENT DOCUMENTS

| | | |
|---|---|---|
| 2,910,978 A | 11/1959 | Urist |
| 3,584,318 A | 6/1971 | Scales et al. |
| 3,744,061 A | 7/1973 | Frost |
| 3,806,960 A | 4/1974 | Weber |
| 3,818,512 A | 6/1974 | Shersher |

(Continued)

FOREIGN PATENT DOCUMENTS

| | | |
|---|---|---|
| AU | 770273 B2 | 2/2004 |
| AU | 2003266434 A1 | 7/2004 |

(Continued)

OTHER PUBLICATIONS

"ANCA-FIT," brochure. Cremascoli Ortho Group. (undated) 7 sheets.

(Continued)

*Primary Examiner* — Bruce E Snow

(74) *Attorney, Agent, or Firm* — Schwegman Lundberg & Woessner, P.A.

(57) ABSTRACT

A prosthesis to replace a portion of the anatomy, such as the acetabulum, can include a first portion. A second prosthesis portion can be positioned relative to the shell to provide the bearing surface to articulate with a femoral head prosthesis or femoral head. The second prosthesis portion can include a connection portion to engage a connection portion in the shell.

6 Claims, 15 Drawing Sheets

(56) References Cited

U.S. PATENT DOCUMENTS 3,859,669 A 1/1975 Shersher
3,894,297 A 7/1975 Mittelmeier et al.
4,001,897 A 1/1977 Rambert et al.
4,031,570 A 6/1977 Frey
4,058,856 A 11/1977 Doerre et al.
D249,957 S 10/1978 Eicher et al.
4,172,296 A 10/1979 D'Errico
4,241,463 A 12/1980 Khovaylo
4,408,360 A 10/1983 Keller
4,596,580 A 6/1986 Weill
4,624,674 A 11/1986 Pappas et al.
4,650,491 A 3/1987 Parchinski
4,666,448 A 5/1987 Ganz
4,666,450 A 5/1987 Kenna
4,676,798 A 6/1987 Noiles
4,676,799 A 6/1987 Legrand
4,678,472 A 7/1987 Noiles
4,681,589 A 7/1987 Tronzo
4,687,487 A 8/1987 Hintermann
4,693,986 A 9/1987 Vit et al.
4,695,282 A 9/1987 Forte et al.
4,704,127 A 11/1987 Averill et al.
4,714,477 A 12/1987 Fichera et al.
4,715,859 A 12/1987 Schelhas et al.
4,715,860 A 12/1987 Amstutz et al.
4,716,894 A 1/1988 Lazzeri et al.
4,718,911 A 1/1988 Kenna
4,737,411 A 4/1988 Graves, Jr. et al.
4,743,262 A 5/1988 Tronzo
4,770,658 A 9/1988 Geremakis
4,770,659 A 9/1988 Kendall
4,784,662 A 11/1988 Muller
4,784,663 A 11/1988 Kenna
4,792,337 A 12/1988 Muller
4,795,469 A 1/1989 Oh
4,795,471 A 1/1989 Oh
4,801,301 A 1/1989 Noiles
4,813,961 A 3/1989 Sostegni
4,822,369 A 4/1989 Oueveau et al.
4,828,565 A 5/1989 Duthoit et al.
4,840,630 A 6/1989 Kitamura
4,840,632 A 6/1989 Kampner
4,841,975 A 6/1989 Woolson
4,851,006 A 7/1989 Tuke
4,871,368 A 10/1989 Wagner
4,878,916 A 11/1989 Rhenter et al.
4,883,491 A 11/1989 Mallory et al.
4,892,549 A 1/1990 Figgie, III et al.
4,904,265 A 2/1990 MacCollum et al.
4,908,033 A 3/1990 Frey et al.
4,911,723 A 3/1990 Menschik
4,919,674 A 4/1990 Schelhas
4,921,500 A 5/1990 Averill et al.
4,923,473 A 5/1990 Griss et al.
4,936,855 A 6/1990 Sherman
4,936,856 A 6/1990 Keller
4,936,861 A 6/1990 Muller et al.
4,950,299 A 8/1990 Noiles
4,955,325 A 9/1990 Zarnowski et al.
4,955,917 A 9/1990 Karpf
4,957,510 A 9/1990 Cremascoli
4,960,427 A 10/1990 Noiles
4,963,154 A 10/1990 Anapliotis et al.
4,969,910 A 11/1990 Frey et al.
4,978,356 A 12/1990 Noiles
4,994,064 A 2/1991 Aboczky
5,002,577 A 3/1991 Bolesky et al.
5,007,933 A 4/1991 Sidebotham et al.
5,019,105 A 5/1991 Wiley
5,021,062 A 6/1991 Adrey et al.
5,021,063 A 6/1991 Tager
5,030,221 A 7/1991 Buechel et al.
5,037,424 A 8/1991 Aboczsky
5,041,140 A 8/1991 Teinturier
5,049,158 A 9/1991 Engelhardt et al.
5,061,270 A 10/1991 Aboczky
5,062,853 A 11/1991 Forte
5,080,677 A 1/1992 Shelley
5,080,678 A 1/1992 Spotorno et al.
5,092,897 A 3/1992 Forte
5,092,898 A 3/1992 Bekki et al.
5,098,437 A 3/1992 Kashuba et al.
5,108,445 A 4/1992 Ashby
5,108,446 A 4/1992 Wagner et al.
5,108,447 A 4/1992 Zeiler et al.
5,108,448 A 4/1992 Gautier
5,116,339 A 5/1992 Glock
5,133,763 A 7/1992 Mullers
5,133,764 A 7/1992 Pappas et al.
5,147,407 A 9/1992 Tager
5,156,626 A 10/1992 Broderick et al.
5,169,399 A 12/1992 Ryland et al.
5,169,400 A 12/1992 Muhling et al.
5,171,285 A 12/1992 Broderick
5,171,286 A 12/1992 Lawes et al.
5,180,394 A 1/1993 Davidson
5,192,325 A 3/1993 Kijima et al.
5,222,984 A 6/1993 Forte
5,226,917 A 7/1993 Schryver
5,263,988 A 11/1993 Huebner
5,275,601 A 1/1994 Gogolewski et al.
5,282,864 A 2/1994 Noiles et al.
5,284,483 A 2/1994 Johnson et al.
5,310,408 A 5/1994 Schryver et al.
5,314,479 A 5/1994 Rockwood, Jr. et al.
5,314,487 A 5/1994 Schryver et al.
5,314,491 A 5/1994 Thongpreda et al.
5,326,368 A 7/1994 Collazo
5,358,532 A 10/1994 Evans et al.
5,360,451 A 11/1994 Keller
5,360,452 A 11/1994 Engelhardt et al.
5,364,403 A 11/1994 Petersen et al.
5,370,702 A 12/1994 Jones
5,376,122 A 12/1994 Pappas et al.
5,383,938 A 1/1995 Rohr et al.
5,405,392 A 4/1995 Deckner
5,405,502 A 4/1995 Palmu et al.
5,413,603 A 5/1995 Noiles et al.
5,417,696 A 5/1995 Kashuba et al.
5,425,778 A 6/1995 Zichner et al.
5,425,779 A 6/1995 Schlosser et al.
5,431,657 A 7/1995 Rohr
5,443,519 A 8/1995 Averill et al.
5,458,649 A 10/1995 Spotorno et al.
5,458,650 A 10/1995 Carret et al.
5,474,560 A 12/1995 Rohr, Jr.
5,480,448 A 1/1996 Mikhail
5,486,181 A 1/1996 Cohen et al.
5,507,824 A 4/1996 Lennox
5,507,825 A 4/1996 Frei
5,507,826 A 4/1996 Besselink et al.
5,507,828 A 4/1996 Maumy et al.
5,520,985 A 5/1996 Helicher
5,527,317 A 6/1996 Ashby et al.
5,534,027 A 7/1996 Hodorek
5,540,697 A 7/1996 Rehmann et al.
5,549,681 A 8/1996 Segmuller et al.
5,549,693 A 8/1996 Roux et al.
5,549,694 A 8/1996 Noiles et al.
5,549,696 A 8/1996 Willi
5,549,697 A 8/1996 Caldarise
5,549,698 A 8/1996 Averill et al.
5,549,699 A 8/1996 MacMahon et al.
5,549,700 A 8/1996 Graham et al.
5,549,701 A 8/1996 Mikhail
5,571,198 A 11/1996 Drucker et al.
5,571,200 A 11/1996 Cohen et al.
5,571,201 A 11/1996 Averill et al.
5,577,368 A 11/1996 Hamilton et al.
5,584,837 A 12/1996 Petersen
5,593,445 A 1/1997 Waits
5,609,647 A 3/1997 K alberer et al.
5,609,648 A 3/1997 Oehy et al.
5,624,464 A 4/1997 Wagner et al.

(56) References Cited

U.S. PATENT DOCUMENTS 5,639,280 A 6/1997 Warner et al.
5,641,323 A 6/1997 Caldarise
5,645,594 A 7/1997 Devanathan et al.
5,645,601 A 7/1997 Pope et al.
5,645,606 A 7/1997 Oehy et al.
5,658,294 A 8/1997 Sederholm
5,658,338 A 8/1997 Tullos et al.
5,658,345 A 8/1997 Willi
5,658,346 A 8/1997 Willi
5,658,347 A 8/1997 Sarkisian et al.
5,658,348 A 8/1997 Rohr, Jr.
5,665,119 A 9/1997 Koller
5,676,704 A 10/1997 Ries et al.
5,690,632 A 11/1997 Schwartz et al.
5,702,448 A 12/1997 Buechel et al.
5,702,456 A 12/1997 Pienkowski
5,702,473 A 12/1997 Albrektsson et al.
5,702,475 A 12/1997 Zahedi
5,702,476 A 12/1997 Limacher et al.
5,702,477 A 12/1997 Capello et al.
5,702,478 A 12/1997 Tornier
5,702,483 A 12/1997 Kwong
5,711,973 A 1/1998 Rothschild et al.
5,716,414 A 2/1998 Caldarise
5,725,580 A 3/1998 Cloutier et al.
5,725,587 A 3/1998 Garber
5,725,588 A 3/1998 Errico et al.
5,725,589 A 3/1998 Pfaff et al.
5,725,591 A 3/1998 DeCarlo, Jr. et al.
5,752,958 A 5/1998 Wellisz
5,755,799 A 5/1998 Oehy et al.
5,755,803 A 5/1998 Haines et al.
5,755,806 A 5/1998 Stalcup et al.
5,755,808 A 5/1998 DeCarlo et al.
5,756,027 A 5/1998 Rothschild et al.
5,766,260 A 6/1998 Whiteside
5,766,280 A 6/1998 Hallqvist et al.
5,768,134 A 6/1998 Swaelens et al.
5,782,928 A 7/1998 Ries et al.
5,782,929 A 7/1998 Sederholm
5,782,930 A 7/1998 Lin et al.
5,788,916 A 8/1998 Caldarise
5,800,555 A 9/1998 Gray, III
5,824,107 A 10/1998 Tschirren
5,824,108 A 10/1998 Huebner
5,830,215 A 11/1998 Incavo et al.
5,871,547 A 2/1999 Abouaf et al.
5,871,548 A 2/1999 Sanders et al.
5,879,297 A 3/1999 Haynor et al.
5,879,397 A 3/1999 Kalberer et al.
5,879,398 A 3/1999 Swarts et al.
5,879,399 A 3/1999 Church
5,879,400 A 3/1999 Merrill et al.
5,879,401 A 3/1999 Besemer et al.
5,879,402 A 3/1999 Lawes et al.
5,879,404 A 3/1999 Bateman et al.
5,879,405 A 3/1999 Ries et al.
5,879,406 A 3/1999 Lilley
5,879,407 A 3/1999 Waggener
5,885,299 A 3/1999 Winslow et al.
5,888,204 A 3/1999 Ralph et al.
5,888,205 A 3/1999 Pratt et al.
5,897,592 A 4/1999 Caldarise et al.
5,904,688 A 5/1999 Gilbert et al.
5,904,720 A 5/1999 Farrar et al.
5,916,268 A 6/1999 Schollner et al.
5,916,270 A 6/1999 Lipman
5,919,236 A 7/1999 Pfaff et al.
5,931,870 A 8/1999 Cuckler et al.
5,935,175 A 8/1999 Ostiguy, Jr. et al.
5,938,701 A 8/1999 Hiernard et al.
5,938,702 A 8/1999 Lopez et al.
5,964,809 A 10/1999 Lin et al.
5,972,032 A 10/1999 Lopez et al.
5,989,293 A 11/1999 Cook et al.
5,989,294 A 11/1999 Marlow
5,997,579 A 12/1999 Albrektsson et al.
6,013,082 A 1/2000 Hiernard et al.
6,013,104 A 1/2000 Kampner
6,022,357 A 2/2000 Reu et al.
6,027,505 A 2/2000 Peter et al.
6,045,583 A 4/2000 Gross et al.
6,051,751 A 4/2000 Sioshansi et al.
6,059,833 A 5/2000 Doets
6,063,123 A 5/2000 Burrows et al.
6,063,124 A 5/2000 Amstutz
6,087,553 A 7/2000 Cohen et al.
6,093,208 A 7/2000 Tian
6,096,083 A 8/2000 Keller et al.
6,102,951 A 8/2000 Sutter et al.
6,105,235 A 8/2000 Caldarise
6,120,545 A 9/2000 Hamelijnck et al.
6,120,546 A 9/2000 Dye et al.
6,126,695 A 10/2000 Semlitsch
6,129,730 A 10/2000 Bono et al.
6,129,765 A 10/2000 Lopez et al.
6,136,033 A 10/2000 Suemer
6,136,034 A 10/2000 Townley
6,139,582 A 10/2000 DeCarlo, Jr. et al.
6,152,930 A 11/2000 Mastrorio
6,152,961 A 11/2000 Ostiguy, Jr. et al.
6,152,962 A 11/2000 DeCarlo, Jr.
6,162,256 A 12/2000 Ostiguy, Jr. et al.
6,162,856 A 12/2000 Crompton et al.
6,165,220 A 12/2000 McKellop et al.
6,206,881 B1 3/2001 Frigg et al.
6,206,929 B1 3/2001 Ochoa et al.
6,217,615 B1 4/2001 Sioshansi et al.
6,224,096 B1 5/2001 Katsuda et al.
6,224,633 B1 5/2001 Kalberer et al.
6,228,121 B1 5/2001 Khalili
6,231,612 B1 5/2001 Balay et al.
6,238,435 B1 5/2001 Meulink et al.
6,241,773 B1 6/2001 Tashima et al.
6,248,132 B1 6/2001 Harris
6,250,494 B1 6/2001 Diamond
6,280,476 B1 8/2001 Metzger et al.
6,306,140 B1 10/2001 Siddiqui
6,319,257 B1 11/2001 Carignan et al.
6,319,285 B1 11/2001 Chamier et al.
6,334,875 B1 1/2002 Keller
6,352,559 B1 3/2002 Church
6,355,043 B1 3/2002 Adam
6,358,282 B1 3/2002 Wymann
6,368,354 B2 4/2002 Burstein et al.
6,379,389 B1 4/2002 Koch
6,387,132 B1 5/2002 Deppisch et al.
6,395,005 B1 5/2002 Lovell
6,416,553 B1 7/2002 White et al.
6,420,568 B1 7/2002 Matson et al.
6,425,921 B1 7/2002 Grundei et al.
6,447,550 B1 9/2002 Hunter et al.
6,454,809 B1 9/2002 Tornier
6,468,281 B1 10/2002 Badorf et al.
6,475,243 B1 11/2002 Sheldon et al.
6,488,713 B1 12/2002 Hershberger
6,488,715 B1 12/2002 Pope et al.
6,517,583 B1 2/2003 Pope et al.
6,520,995 B2 2/2003 Church
6,527,808 B1 3/2003 Albertorio et al.
6,527,809 B1 3/2003 Doursounian et al.
6,537,321 B1 3/2003 Horber
6,558,794 B1 5/2003 Fehrenbacher et al.
6,575,980 B1 6/2003 Robie et al.
6,589,284 B1 7/2003 Silberer
6,609,599 B1 8/2003 Chang
6,609,621 B2 8/2003 Denny et al.
6,610,097 B2 8/2003 Serbousek et al.
6,610,257 B2 8/2003 Vane
6,611,636 B2 8/2003 Deliwala
6,611,816 B2 8/2003 Lebda et al.
6,611,862 B2 8/2003 Reisman
6,611,973 B2 9/2003 Connell
6,612,256 B1 9/2003 Martin

(56) References Cited

U.S. PATENT DOCUMENTS 6,612,384 B1 9/2003 Singh et al.
6,612,417 B2 9/2003 Garvey
6,612,425 B1 9/2003 Garvey
6,612,430 B1 9/2003 Silvera
6,612,545 B1 9/2003 Rutter et al.
6,612,649 B2 9/2003 Kain
6,612,713 B1 9/2003 Kuelbs
6,612,766 B2 9/2003 Collins
6,613,235 B1 9/2003 Anderson, Jr. et al.
6,615,535 B2 9/2003 Snell et al.
6,615,756 B2 9/2003 Barrus
6,615,766 B1 9/2003 Curry
6,616,310 B1 9/2003 Marsh
6,616,498 B1 9/2003 Thai
6,616,924 B1 9/2003 Chastain
6,618,047 B1 9/2003 Lim
6,618,157 B2 9/2003 Coyle et al.
6,618,753 B2 9/2003 Holland et al.
6,618,806 B1 9/2003 Brown et al.
6,619,167 B2 9/2003 Mikkelsen et al.
6,619,168 B2 9/2003 Alsten et al.
6,619,235 B2 9/2003 Woytowitz, Jr.
6,619,331 B1 9/2003 Suchdev
6,619,594 B2 9/2003 Wolf et al.
6,619,603 B1 9/2003 Recknagel et al.
6,619,808 B1 9/2003 Pelto
6,619,816 B1 9/2003 Johnson
6,620,016 B1 9/2003 Thai
6,620,046 B2 9/2003 Rowe
6,620,319 B2 9/2003 Behmann et al.
6,621,083 B2 9/2003 Cole
6,621,172 B2 9/2003 Nakayama et al.
6,621,515 B2 9/2003 Matthews et al.
6,621,834 B1 9/2003 Scherpbier et al.
6,622,128 B1 9/2003 Bedell et al.
6,622,327 B1 9/2003 Rivera
6,622,328 B2 9/2003 Rivera
6,622,350 B2 9/2003 Austin et al.
6,622,414 B1 9/2003 Oliver et al.
6,622,858 B1 9/2003 Wilkinson et al.
6,623,354 B2 9/2003 Morris et al.
6,626,913 B1 9/2003 McKinnon et al.
6,626,947 B2 9/2003 Lester et al.
6,638,311 B2 10/2003 Wang et al.
6,641,617 B1 11/2003 Merrill et al.
6,652,533 B2 11/2003 O'Neil
6,652,586 B2 11/2003 Hunter et al.
6,660,040 B2 12/2003 Chan et al.
RE38,409 E 1/2004 Noiles
6,676,706 B1 1/2004 Mears et al.
6,682,566 B2 1/2004 Draenert
6,706,071 B1 3/2004 Wolter
6,709,462 B2 3/2004 Hanssen
6,712,857 B1 3/2004 Roger
6,726,725 B2 4/2004 Hunter et al.
6,730,091 B1 5/2004 Pfefferle et al.
6,746,454 B2 6/2004 Winterbottom et al.
6,755,835 B2 6/2004 Schultheiss et al.
6,758,864 B2 7/2004 Storer et al.
6,761,741 B2 7/2004 Iesaka
6,797,007 B1 9/2004 Von Chamier et al.
6,811,569 B1 11/2004 Afriat et al.
6,821,278 B2 11/2004 Frigg et al.
6,827,742 B2 12/2004 Hayes, Jr. et al.
6,860,903 B2 3/2005 Mears et al.
6,866,685 B2 3/2005 Chan et al.
6,881,229 B2 4/2005 Khandkar et al.
6,916,342 B2 7/2005 Frederick et al.
6,926,740 B2 8/2005 Lewis et al.
7,160,332 B2 1/2007 Frederick et al.
7,264,636 B2 9/2007 Lewis et al.
7,294,150 B1 11/2007 Mandell et al.
RE40,090 E 2/2008 Whiteside
7,326,253 B2 2/2008 Synder et al.
7,507,063 B2 3/2009 Dexter et al.
7,794,504 B2 9/2010 Case
7,819,925 B2 10/2010 King et al.
7,955,395 B2 6/2011 Shea et al.
8,123,815 B2 2/2012 Meridew et al.
8,308,810 B2 11/2012 Meridew
8,556,985 B2 10/2013 Meridew
2001/0037156 A1 11/2001 Burstein et al.
2001/0051830 A1 12/2001 Tuke et al.
2002/0040244 A1 4/2002 Despres et al.
2002/0040245 A1 4/2002 Lester et al.
2002/0045901 A1 4/2002 Wagner et al.
2002/0049500 A1 4/2002 Draenert
2002/0052659 A1 5/2002 Hayes et al.
2002/0058988 A1 5/2002 Fischell et al.
2002/0058998 A1 5/2002 Church
2002/0068980 A1 6/2002 Serbousek et al.
2002/0107577 A1 8/2002 Storer et al.
2002/0111691 A1 8/2002 Wang et al.
2002/0116068 A1 8/2002 McLean
2002/0143402 A1 10/2002 Steinberg
2002/0147499 A1 10/2002 Shea et al.
2002/0156536 A1 10/2002 Harris et al.
2002/0165615 A1 11/2002 Abouaf et al.
2002/0177854 A1 11/2002 Tuke et al.
2003/0050645 A1 3/2003 Parker et al.
2003/0050703 A1 3/2003 Harris et al.
2003/0050705 A1 3/2003 Cueille et al.
2003/0060889 A1 3/2003 Tarabishy
2003/0060890 A1 3/2003 Tarabishy
2003/0105529 A1 6/2003 Synder et al.
2003/0120347 A1 6/2003 Steinberg
2003/0135281 A1 7/2003 Hanssen
2003/0149438 A1 8/2003 Nichols et al.
2003/0153981 A1 8/2003 Wang et al.
2003/0153982 A1 8/2003 Pria
2003/0158559 A1 8/2003 Diaz
2003/0163203 A1 8/2003 Nycz et al.
2003/0171817 A1 9/2003 Rambert et al.
2003/0187512 A1 10/2003 Frederick et al.
2003/0191537 A1 10/2003 Wasielewski
2003/0212458 A1 11/2003 Harris et al.
2003/0229356 A1 12/2003 Dye
2003/0233100 A1 12/2003 Santarella et al.
2004/0002766 A1 1/2004 Hunter et al.
2004/0019380 A1 1/2004 Baege et al.
2004/0023784 A1 2/2004 Yu et al.
2004/0030344 A1 2/2004 Dye et al.
2004/0034352 A1 2/2004 Needham et al.
2004/0054373 A1 3/2004 Serra et al.
2004/0054418 A1 3/2004 McLean et al.
2004/0059427 A1 3/2004 Serbousek et al.
2004/0059429 A1 3/2004 Amin et al.
2004/0073225 A1 4/2004 Subba Rao
2004/0073226 A1 4/2004 Cotting et al.
2004/0088052 A1 5/2004 Dearnaley
2004/0098127 A1 5/2004 Charlebois et al.
2004/0111089 A1 6/2004 Stevens et al.
2004/0122524 A1 6/2004 Hunter et al.
2004/0143341 A1 7/2004 McLean
2004/0158330 A1 8/2004 Muller et al.
2004/0172039 A1 9/2004 Dye
2004/0186586 A1 9/2004 Seyer et al.
2004/0199258 A1 10/2004 Macara
2004/0204767 A1 10/2004 Park et al.
2004/0215200 A1 10/2004 Tornier et al.
2004/0220679 A1 11/2004 Diaz et al.
2004/0225369 A1 11/2004 Lakin et al.
2004/0225370 A1 11/2004 Cruchet et al.
2004/0225371 A1 11/2004 Roger
2004/0236341 A1 11/2004 Petersen
2004/0241314 A1 12/2004 Li
2004/0267373 A1 12/2004 Dwyer et al.
2004/0267376 A1 12/2004 Suzuki et al.
2005/0004678 A1 1/2005 Richards
2005/0010303 A1 1/2005 Nogier
2005/0033442 A1 2/2005 Fisher et al.
2005/0033445 A1 2/2005 Siebel
2005/0060040 A1 3/2005 Auxepaules et al.
2005/0065527 A1 3/2005 Justin

(56) References Cited

U.S. PATENT DOCUMENTS

| | | | |
|---|---|---|---|
| 2005/0070904 | A1 | 3/2005 | Gerlach et al. |
| 2005/0071015 | A1 | 3/2005 | Sekel |
| 2005/0080490 | A1 | 4/2005 | Bertram |
| 2005/0085820 | A1 | 4/2005 | Collins et al. |
| 2005/0085823 | A1 | 4/2005 | Murphy |
| 2005/0087915 | A1 | 4/2005 | Pope et al. |
| 2005/0090903 | A1 | 4/2005 | Khandkar et al. |
| 2005/0102034 | A1 | 5/2005 | Hayes et al. |
| 2005/0102035 | A1 | 5/2005 | Grundei |
| 2005/0240276 | A1 | 10/2005 | Shea et al. |
| 2005/0246031 | A1 | 11/2005 | Frederick et al. |
| 2006/0004463 | A1 | 1/2006 | Lewis et al. |
| 2006/0178750 | A1 | 8/2006 | Chieng |
| 2006/0229731 | A1 | 10/2006 | Newsome et al. |
| 2006/0276905 | A1 | 12/2006 | Calamel |
| 2007/0106352 | A1 | 5/2007 | Carstens |
| 2007/0106392 | A1 | 5/2007 | Servidio et al. |
| 2007/0173948 | A1 | 7/2007 | Meridew et al. |
| 2007/0203583 | A1 | 8/2007 | Slone |
| 2007/0203585 | A1 | 8/2007 | Wilson |
| 2007/0239283 | A1 | 10/2007 | Berger et al. |
| 2008/0140215 | A1 | 6/2008 | Gladdish et al. |
| 2008/0288081 | A1 | 11/2008 | Scrafton et al. |
| 2009/0008886 | A1 | 1/2009 | Shu |
| 2009/0088865 | A1 | 4/2009 | Brehm |
| 2009/0101776 | A1 | 4/2009 | Peterson et al. |
| 2009/0287312 | A1 | 11/2009 | Berger et al. |
| 2010/0262144 | A1 | 10/2010 | Kelman et al. |
| 2011/0009975 | A1 | 1/2011 | Allen et al. |
| 2011/0015752 | A1 | 1/2011 | Meridew |
| 2011/0015753 | A1 | 1/2011 | Meridew |
| 2011/0087335 | A1 | 4/2011 | Newsome et al. |
| 2013/0073051 | A1 | 3/2013 | Meridew |

FOREIGN PATENT DOCUMENTS

| | | | |
|---|---|---|---|
| AU | 781574 | B2 | 6/2005 |
| AU | 2005221715 | A1 | 9/2005 |
| AU | 783205 | B2 | 10/2005 |
| AU | 2002336155 | B2 | 11/2006 |
| AU | 2006340337 | A1 | 9/2007 |
| AU | 2007333133 | A1 | 6/2008 |
| AU | 2002302005 | B2 | 8/2008 |
| AU | 2008218993 | A1 | 8/2008 |
| AU | 2008242972 | A1 | 10/2008 |
| AU | 2009202628 | A1 | 1/2010 |
| AU | 2009286494 | A1 | 3/2010 |
| CA | 2061183 | A1 | 8/1992 |
| CA | 2314497 | A1 | 6/1999 |
| CH | 554668 | A | 10/1974 |
| DE | 1975536 | U | 12/1967 |
| DE | 2950536 | A1 | 7/1981 |
| DE | 8500869 | U1 | 12/1985 |
| DE | 3535959 | C1 | 4/1987 |
| DE | 3726213 | A1 | 2/1989 |
| DE | 4102510 | A1 | 7/1992 |
| DE | 4106272 | A1 | 9/1992 |
| DE | 9208752 | U1 | 12/1992 |
| DE | 4128259 | A1 | 3/1993 |
| DE | 4142920 | A1 | 7/1993 |
| DE | 4211345 | C1 | 11/1993 |
| DE | 4219939 | A1 | 12/1993 |
| DE | 4222218 | A1 | 1/1994 |
| DE | 4304022 | A1 | 8/1994 |
| DE | 9418900 | U1 | 1/1995 |
| DE | 4325701 | A1 | 2/1995 |
| DE | 4336552 | C1 | 3/1995 |
| DE | 4335931 | A1 | 4/1995 |
| DE | 29516473 | U1 | 12/1995 |
| DE | 29517637 | U1 | 1/1996 |
| DE | 19616058 | A1 | 10/1997 |
| DE | 19616059 | A1 | 10/1997 |
| DE | 19620750 | C1 | 1/1998 |
| DE | 19701536 | A1 | 2/1998 |
| DE | 19654409 | C1 | 4/1998 |
| DE | 19701778 | A1 | 6/1998 |
| DE | 19755776 | A1 | 7/1999 |
| DE | 19755246 | C1 | 3/2000 |
| DE | 19919083 | C1 | 12/2000 |
| DE | 20201785 | U1 | 6/2002 |
| DE | 102010001600 | A1 | 8/2010 |
| EP | 0066092 | A1 | 12/1982 |
| EP | 0091315 | A1 | 10/1983 |
| EP | 0137664 | A2 | 4/1985 |
| EP | 0139356 | A1 | 5/1985 |
| EP | 169978 | A1 | 2/1986 |
| EP | 0190093 | A1 | 8/1986 |
| EP | 0208578 | A1 | 1/1987 |
| EP | 0214885 | | 3/1987 |
| EP | 0239210 | A1 | 9/1987 |
| EP | 0239485 | A2 | 9/1987 |
| EP | 0245527 | A1 | 11/1987 |
| EP | 0265712 | A1 | 5/1988 |
| EP | 0270744 | A1 | 6/1988 |
| EP | 0297789 | A1 | 1/1989 |
| EP | 0302850 | A2 | 2/1989 |
| EP | 0313762 | A1 | 5/1989 |
| EP | 0315795 | A1 | 5/1989 |
| EP | 0329019 | A1 | 8/1989 |
| EP | 0341199 | A1 | 11/1989 |
| EP | 0346270 | A1 | 12/1989 |
| EP | 0357302 | A1 | 3/1990 |
| EP | 0402810 | A1 | 12/1990 |
| EP | 0404680 | A1 | 12/1990 |
| EP | 0407332 | A1 | 1/1991 |
| EP | 0436317 | A1 | 7/1991 |
| EP | 0444381 | A1 | 9/1991 |
| EP | 0453694 | A1 | 10/1991 |
| EP | 0482320 | A1 | 4/1992 |
| EP | 0485678 | A1 | 5/1992 |
| EP | 0488943 | A1 | 6/1992 |
| EP | 0498685 | A1 | 8/1992 |
| EP | 0501207 | A1 | 9/1992 |
| EP | 0554214 | A1 | 8/1993 |
| EP | 0578322 | A2 | 1/1994 |
| EP | 0578345 | A1 | 1/1994 |
| EP | 0586335 | A1 | 3/1994 |
| EP | 0610146 | A1 | 8/1994 |
| EP | 0636351 | A2 | 2/1995 |
| EP | 0639357 | A1 | 2/1995 |
| EP | 0645984 | A1 | 4/1995 |
| EP | 0648478 | | 4/1995 |
| EP | 0649641 | A2 | 4/1995 |
| EP | 0654255 | A1 | 5/1995 |
| EP | 0663193 | A1 | 7/1995 |
| EP | 0680735 | A2 | 11/1995 |
| EP | 0694294 | A1 | 1/1996 |
| EP | 0699425 | A1 | 3/1996 |
| EP | 0714644 | A1 | 6/1996 |
| EP | 0722703 | A2 | 7/1996 |
| EP | 0726066 | A2 | 8/1996 |
| EP | 0728448 | A1 | 8/1996 |
| EP | 0743049 | A1 | 11/1996 |
| EP | 0743050 | A1 | 11/1996 |
| EP | 0771552 | A1 | 5/1997 |
| EP | 0773007 | A1 | 5/1997 |
| EP | 0826347 | A1 | 3/1998 |
| EP | 0841041 | A2 | 5/1998 |
| EP | 092754 7 | A2 | 7/1999 |
| EP | 0927547 | A2 | 7/1999 |
| EP | 0927548 | A2 | 7/1999 |
| EP | 0941718 | A2 | 9/1999 |
| EP | 0944368 | A1 | 9/1999 |
| EP | 0945109 | A2 | 9/1999 |
| EP | 0949891 | A1 | 10/1999 |
| EP | 0958797 | A1 | 11/1999 |
| EP | 0995412 | A1 | 4/2000 |
| EP | 1013241 | A2 | 6/2000 |
| EP | 1052949 | A1 | 11/2000 |
| EP | 1066806 | A1 | 1/2001 |
| EP | 1086666 | A1 | 3/2001 |
| EP | 1098611 | A1 | 5/2001 |
| EP | 1308141 | A1 | 5/2003 |
| EP | 1312323 | A2 | 5/2003 |

(56) References Cited

FOREIGN PATENT DOCUMENTS

| | | | |
|---|---|---|---|
| EP | 1336394 | A1 | 8/2003 |
| EP | 1395206 | A1 | 3/2004 |
| EP | 1610729 | A1 | 1/2006 |
| EP | 1631219 | A2 | 3/2006 |
| EP | 1712206 | A2 | 10/2006 |
| EP | 1813227 | A2 | 8/2007 |
| EP | 1825834 | | 8/2007 |
| EP | 2193764 | A1 | 6/2010 |
| FR | 2419717 | A1 | 10/1979 |
| FR | 2592787 | A1 | 7/1987 |
| FR | 2597329 | A1 | 10/1987 |
| FR | 2617040 | A1 | 12/1988 |
| FR | 2628314 | A1 | 9/1989 |
| FR | 2628967 | A1 | 9/1989 |
| FR | 2631542 | A1 | 11/1989 |
| FR | 2638963 | A1 | 5/1990 |
| FR | 2648703 | A1 | 12/1990 |
| FR | 2653326 | A1 | 4/1991 |
| FR | 2661605 | A1 | 11/1991 |
| FR | 2668055 | A1 | 4/1992 |
| FR | 2668057 | A1 | 4/1992 |
| FR | 2668923 | A1 | 5/1992 |
| FR | 2680674 | A1 | 3/1993 |
| FR | 2682588 | A1 | 4/1993 |
| FR | 2684544 | A1 | 6/1993 |
| FR | 2699067 | A1 | 6/1994 |
| FR | 2700686 | A1 | 7/1994 |
| FR | 2700946 | A1 | 8/1994 |
| FR | 2708459 | A1 | 2/1995 |
| FR | 2715828 | A3 | 8/1995 |
| FR | 2719761 | A1 | 11/1995 |
| FR | 2728157 | A1 | 6/1996 |
| FR | 2748654 | A1 | 11/1997 |
| FR | 2748655 | A1 | 11/1997 |
| FR | 2793137 | A1 | 11/2000 |
| FR | 2824258 | A1 | 11/2002 |
| FR | 2846225 | A1 | 4/2004 |
| FR | 2847801 | A1 | 6/2004 |
| FR | 2897527 | A1 | 8/2007 |
| GB | 1245451 | A | 9/1971 |
| GB | 2029229 | A | 3/1980 |
| GB | 2316873 | A | 3/1998 |
| GB | 2358353 | A | 7/2001 |
| GB | 2365343 | A | 2/2002 |
| GB | 2463066 | A | 3/2010 |
| JP | 54127195 | A | 10/1979 |
| JP | 1136654 | A | 5/1989 |
| JP | 2161943 | A | 6/1990 |
| JP | 3029650 | A | 2/1991 |
| JP | 5068690 | A | 3/1993 |
| JP | 5137738 | A | 6/1993 |
| JP | 5208027 | A | 8/1993 |
| JP | 716248 | | 1/1995 |
| JP | 7144004 | A | 6/1995 |
| JP | 10146351 | A | 6/1998 |
| JP | 10216162 | A | 8/1998 |
| JP | 11253470 | A | 9/1999 |
| JP | 11313843 | A | 11/1999 |
| JP | 11347055 | | 12/1999 |
| JP | 2001286496 | A | 10/2001 |
| JP | 2009530021 | A | 8/2009 |
| WO | WO-8602261 | A1 | 4/1986 |
| WO | WO-9218067 | A1 | 10/1992 |
| WO | WO-9222265 | A1 | 12/1992 |
| WO | WO-9325157 | A1 | 12/1993 |
| WO | WO-9405234 | A1 | 3/1994 |
| WO | WO-9423670 | A1 | 10/1994 |
| WO | WO-9516413 | A1 | 6/1995 |
| WO | WO-9517140 | A1 | 6/1995 |
| WO | WO-9522944 | A1 | 8/1995 |
| WO | WO-9523566 | A1 | 9/1995 |
| WO | WO-9604862 | A1 | 2/1996 |
| WO | WO-9604866 | A1 | 2/1996 |
| WO | WO-9604867 | A1 | 2/1996 |
| WO | WO-9613231 | A1 | 5/1996 |
| WO | WO-9623457 | A1 | 8/1996 |
| WO | WO-9717040 | A1 | 5/1997 |
| WO | WO-9742913 | A1 | 11/1997 |
| WO | WO-9815240 | A1 | 4/1998 |
| WO | WO-9822049 | A1 | 5/1998 |
| WO | WO-9922674 | A1 | 5/1999 |
| WO | WO-9925276 | A1 | 5/1999 |
| WO | WO-9930634 | A2 | 6/1999 |
| WO | WO-9960955 | A1 | 12/1999 |
| WO | WO-0009045 | A1 | 2/2000 |
| WO | WO-0045748 | A1 | 8/2000 |
| WO | WO-0076427 | A1 | 12/2000 |
| WO | WO-0124739 | A2 | 4/2001 |
| WO | WO-0132108 | A1 | 5/2001 |
| WO | WO-0176511 | A1 | 10/2001 |
| WO | WO-02102285 | A1 | 12/2002 |
| WO | WO-03011116 | A2 | 2/2003 |
| WO | WO-03047470 | A2 | 6/2003 |
| WO | WO-2004084772 | A1 | 10/2004 |
| WO | WO-2004110318 | A2 | 12/2004 |
| WO | WO-2005087141 | A2 | 9/2005 |
| WO | WO-2007056678 | A2 | 5/2007 |
| WO | WO-2007108848 | A1 | 9/2007 |
| WO | WO-2007121167 | A1 | 10/2007 |
| WO | WO-2008073946 | A2 | 6/2008 |
| WO | WO-2008103457 | A2 | 8/2008 |
| WO | WO-2008130989 | A2 | 10/2008 |
| WO | WO-2008146121 | A2 | 12/2008 |
| WO | WO-2009097412 | A2 | 8/2009 |
| WO | WO-2010023447 | A1 | 3/2010 |
| WO | WO-2010060071 | A1 | 5/2010 |
| WO | WO-2011008757 | A1 | 1/2011 |

OTHER PUBLICATIONS

"BIOLOX® delta, A new ceramic in Orthopaedics," brochure. CeramTec. Printed in Germany (undated) 8 sheets.

"BIOLOX® forte ball heads and cup inserts for hip arthroplasty," brochure. (undated) CeramTec AG Printed in Germany.

"BIOLOX® forte," brochure. CeramTec. Printed in Germany (undated) 53 sheets.

"Book of Abstracts" (May 29-Jun. 1, 2002) Central European Orthopaedic Congress CEOC 4th, Zagreb, Croatia pp. 1-196.

"CERAFIT Composant de frottement alumine-alumine," Revue de Chirurgie Orthopédique et réparatrice de l'appareil moteur, Organe de la Société Française de Chirurgie Orthopédique et Traumatologique, (Sep. 1995) vol. 85 No. 5, Ceraver.

"Comparative Analysis Alumina Ceramic versus Zirconia Ceramic, Alumina Ceramic the Gold Standard for 30 Years," (2002) Wright™.

"DePuy Introduces New Metal Head for Hip." http://www.vpico.comarticlemanager/printerfriendly.aspx?article=235071 (Web accessed Apr. 23, 2009) 1 sheet.

"DePuy Orthopaedics Launches Pinnacle™ Hip Solutions with Trueglide™ Technology," Medical News Today (Mar. 10, 2008) http://www.medicalnewstoday.com/printerfriendlynews.php?newsid=100053 (Web accessed Apr. 23, 2009).

"Dynasty™ Acetabular Cup System," Surgical Technique brochure. (2007) Wright Medical Technology, Inc. 24 sheets.

"FriaTep-Vario-System, nach Prof. Dr. Stock," product brochure/catalog (1989).

"Lineage; Ceramic-on-Ceramic Acetabular Cup System," Surgical Technique brochure, (2003) Wright Medical Technology, Inc. 12 sheets.

McTighe, Timothy, "Cementless Modular Stems," (May 2002) JISRE Update. Joint Implant Surgery & Research Foundation 3 sheets.

"Patient Education: Ceramic-on-Ceramic Hip Replacement—Stryker Brochure, The Trident Ceramic Acetabular System," Connecticut Orthopaedic Specialists. http://www.minottiortho.com/pages/ceramic__5.php (Web accessed Apr. 23, 2009) 4 sheets.

"PE Wear is the No 1 Problem of Artificial Hip Joints. The Solution: MonoDome Metal/Metal Articulation," flyer. EMCC Engineering Manufacturing Consulting Corporation AG (SA, Ltd.) 2 sheets (undated).

(56) References Cited

OTHER PUBLICATIONS

"Pinnacle Hip Solutions® , Never Stop Moving™," brochure. Design Rationale (2008) DePuy Orthopaedics, Inc. 34 sheets.
"Pinnacle Hip Solutions® , never stop moving™," brochure. DePuy Orthopaedics, Inc. http://www.hipreplacement.com/DePuy/technology/?printerFriendlyTheme=true (Web accessed Apr. 23, 2009) 2 sheets.
"Plasmacup SC Acetabular Cup," AESCULAP® B.Braun Melsungen AG http://www.bbraun.com/index.cfm?uuid=26EA6AA4838D495B8A895420A83BD099&obj . . . (Web accessed Dec. 5, 2002) 4 sheets.
"Plasmacup® Aesculap Orthopaedics," brochure. Aesculap Implant Systems (Jan. 2008) 16 sheets.
"Plasmacup® SC," AESCULAP Products—Orthopaedics—Joint Implants, http://www.aesculap.com/e/produkte/ot/gelenk_implantate/plasmacup_sc/otp_ps.htm (Web accessed Aug. 15, 2001).
"Plasmacup® SC," AESCULAP® Products—Joint Implants. (2001) http://www.aesculap.de/e/produkte/ot/gelenk_implantate/plasmacup_sc/otp_ps.htm (Web accessed Apr. 14, 2003) 2 sheets.
"PROFEMUR R Revision Prosthesis" brochure. Cremascoli Ortho Group (undated) 9 sheets.
"PROFEMUR™ Total Hip System," Surgical Technique brochure. (2002) Wright Medical Technology pp. 1-24.
"Prospective Sales Agent Information," OTI Osteoimplant Technology, Inc. (Nov. 1999-Oct. 2000) 27 pages.
"Prostheses and Instrumentation, The Furlong® H-A.C. Total Hip Replacment," catalog/brochure. (1987) JRI Joint Replacement Instrumentation Ltd. pp. 1-12 of 16 sheets.
"Signature™ Personalized Patient Care, Surgical Technique Addendum to the Vanguard Knee System" brochure. Biomet® Orthopedics, Inc. (May 15, 2009) pp. 1-8.
"Smith & Nephew launches R3 Acetabular System," press release. http://global.smith-nephew.com/master/news_launch_r3_acetabular_23411.htm (Web accessed Mar. 13, 2008).
"Stanmore Modular Hip System, Timeless Design," brochure. (Sep. 30, 1998) Biomet, Inc. 12 sheets.
"Stryker Trident Hip Implant Component Recall Latest Bad News for Company Since FDA Warning Letter," NewsInferno.com (Jan. 22, 2008) http://www.newsinferno.com/archives/2425 (Web accessed Apr. 23, 2009) 3 sheets.
"The 'triradius' CERAFIT cups: History and concept," CERAVER brochure. http://www.ceraver.fr/anglais/PRODUITS/cotylescerafittriradius.htm (Web accessed Jan. 24, 2003) 1 sheet.
"The Only Answer: CERAFIT and its Alumina-Alumina Combination," brochure. (Apr. 1995) Ceraver Osteal. 11 sheets.
"The Original Furlong Hydroxapatite Ceramic (Osprovit) Coated Total Hip Replacement," brochure. Joint Replacement Instrumentation, Ltd. (1987) 20 sheets.
"Thinking Outside the Cup," Smith & Nephew, Inc. advertisement. (2008) Joint Reconstruction.
"Trident Polyethylene Hip System," 4 individual 1-sheet web pages, Stryker Orthopaedics http:/www.stryker.com/jointreplacements/sites/trident/polyj/innerchange.php (Web accessed Jun. 4, 2015) http:/www.stryker.com/jointreplacements/sites/trident/healthcare/next5.php (Web accessed Jun. 4, 2015) http:/www.france.stryker.com/index/st_pag_medic-home/fr_pag_info-prod/fr_pag_hanche-acetabular-intro/fr_pag_hanche-cup-trident-poly.htm (Web accessed Jun. 4, 2015) http:/www.stryker.com/jointreplacements/sites/trident/poly/ (Web accessed Jun. 4, 2015).
"Trilogy® Acetabular System" brochure. Zimmer (2002) 6 sheets.
"What We Led, What We Said, What We Proved," brochure. (2005) Stryker Orthopaedics. 7 sheets.
"Zimmer® Continuum™ Acetabular System," Surgical Technique brochure. (2009) Zimmer, Inc. 25 sheets.
AESCULAP web page depicting "ceramic on ceramic bearing" http://www.aesculap.com/e/produkte/ot/gelenk_implantate/modular_ker/otp_mod.htm (Web accessed Aug. 15, 2001) 1p.
Antonio, James A. et al., "New Experience with Alumina: Alumina Ceramic Bearings for Total Hip Arthroplasty," (2003) Stryker® Howmedica Osteonics 11 sheets.
BF Cup catalog sheet identifying Axis I and Axis 11 (Jan. 2002) 3 sheets.
Blömer, W., "Biomechanical aspects of modular inlay fixation," (1997) Aesculap, Research and Development, Tuttlingen—Germany. pp. 112-120.
Blömer, W., "Design Aspects fo Modular Inlay Fixation." (Mar. 8, 1997) Performance fo the Wear Couple BIOLOX forte in Hip Arthroplasty, Proceedings of the 2nd Symposium on Ceramic Wear Couple, Stuttgart (Germany) pp. 95-104.
Boehler, M., et al. "Migration Measurement of Cementless Acetabular Components: Value fo Clinical and Radiographic Data," Orthopedics, Migration of Acetabular Components (Aug. 1998) vol. 21 No. 8, pp. 897-900.
Bohler, M., et al., "Comparison of Migration in Modular Sockets with Ceramic and Polyethylene Inlays," Orthopedics, Migration in Modular Sockets (Dec. 2000) vol. 23 No. 12, pp. 1261-1266.
Boutin, P., et al., "The use of dense alumina-alumina ceramic combination in total hip replacement," Journal of Biomedical Materials Research (1988) vol. 22 pp. 1203-1232.
Böhler, M., et al., "Ergebnisse mit der Keramik-KeramikGleitpaarung in der Hiiftendoprothetik", (1996) Proceedings des 1. CERASIV-Symposiums am Mar. 23, 1996 in Stuttgart Herausgegeben von Wolfhart Puhl, 64 Abbildungen . 31 Tabellen pp. 34-38.
Ceraver Osteal brochure for the following products: "The Cerafit Cup"; "The Answer: CERAL Al2O3—Al2O3 Combination"; and "The Cerafit Cup." (1993).
Clarke, Ian C., "Role of Ceramic Implants, Design and Clinical Success with Total Hip Prosthetic Ceramic-to-Ceramic Bearings," Clincal Orthopaedics and Related Research™ (Sep. 1992) No. 282 pp. 19-30.
Department of Health & Human Services 510(I) Summary for DePuy. Trade/Device Name: DePuy Pinnacle® Constrained Acetabular Liner. May 18, 2007 (7 pages).
Diehl, K., et al., "Der zementfreie Hüftgelenkersatz bei Hüftkopfnekrosen mit dem MC-Hüftgelenk," (1991) The Stuhler (Ed.) Hüftkopfnekrose, Springer-Verlag Berlin Heidelberg. 3 sheets.
Effenberger, H., "Hüftendoprothetik, Konstruktion, Klassivation, Implantate, Egrebnisse," (2007) pp. 1-15.
Effenberger, H., et al., "Modifikationen von Form, Material und Modularität der Schraubpfannen," Biomedizinische Technik, Band 47 Heft Jun. 2002 pp. 169-175.
Fuchs, G.A., "2-4 Year Clinical Results with a Ceramic-on-Ceramic_Articulation_in_a_New_Modular_THR-System."
Bioceramics in Hip Joint Replacement (Feb. 2000) pp. 39-45.
Fuchs, G.A., et al., "First 2-5 years results of single designed cemented and noncemented BF prosthesis in total hip arthroplasty." The Orthopedic Journal of China (Sep. 1999) EDIC China, vol. 6 No. 9 pp. 711-715.
Gekeler, J., "Sphärische Press-fit-Pfannen und erste klinische Erfahrungen mit der Keramik-Gleitpaarung (PLASMACUP SC)." Bioceramics in Orthopaedics—New Applications, Proceedings of the 3rd International Symposium on Cerami Wear Couple (Germany) (Feb. 14, 1998) pp. 32-38.
International Preliminary Report on Patentability and Written Opinion mailed Jun. 3, 2011 for PCT/US2009/065651 claiming benefit of U.S. Appl. No. 12/624,142, filed Nov. 23, 2009.
International Search Report and Written Opinion mailed Oct. 14, 2010 claiming benefit of U.S. Appl. No. 12/502,848, filed Jul. 14, 2009.
International Search Report and Written Opinion mailed Mar. 16, 2010 for PCT/US2009/065651 claiming benefit of U.S. Appl. No. 12/624,142, filed Nov. 23, 2009.
Radermacher, "Computer Assisted Orthopaedic Surgery with Image Based Individual Templates," Clinical Orthopaedics and Related Research No. 354, pp. 28-38 (Sep. 1998) Lippincott Williams & Wilkins.
Salzer, M., et al., "A Bioceramic Endoprosthesis for the Replacement of the Proximal Humerus," Archives of Orthopaedic and Traumatic Surgery. (1979) vol. 93 pp. 169-184.

(56) References Cited

OTHER PUBLICATIONS

Salzer, M., et al., Keramische Endoprothesen der oberen Extremität, Z. Orthop. (1975) 113 pp. 458-461.
Scheller, G et al. "MPF Modular Press Fit Cup—the Concept, Experience and First Results." *BIOLOX Symposium*. Georg Thieme Verlag, (2000) pp. 35-38.
Sedel, Laurent, M.D., "Evolution of Alumina-on-Alumina Implants," Clinical Orthopaedics and Related Research (2000) No. 379, pp. 48-54.
Sedel, Laurent, M.D., et al., "Alumina-Alumina Hip Replacement in Patients Younger Than 50 Years Old," Clinical Orthopaedics and Related Research (1994) No. 298, pp. 175-183.
Willmann, G., "Modularity—The Chance to Solve the Wear Problems in Total Hip Replacement." *BIOLOX Symposium*. Ferdinand Enke Verlag, (1996) pp. 94-99.
Willmann, G., et al., "Keramische Pfanneneinsätze für Hüftendoprothesen Teil 2: Bauteilprüfung und -sicherheit; Ceramic Acetabular Cups for Total Hip Replacement Part 2: Component Testing and Reliability," Biomedizinische Technik (1996) Band 41 Heft 10 pp. 284-290.
Willmann, G., et al., "Keramische Pfanneneinsätze für Hüftendoprothesen; Ceramic Cup Inserts for Hip Endoprostheses," Biomedizinische Technik (1996) Band 41 Heft 4 pp. 98-105.
U.S. Appl. No. 12/502,848, Applicant's Summary of Examiner Interview filed Jun. 5, 2012, 1 pg.
U.S. Appl. No. 12/502,848, Examiner Interview Summary mailed May 29, 2012, 3 pgs.
U.S. Appl. No. 12/502,848, Examiner Interview Summary mailed Oct. 18, 2011, 3 pgs.
U.S. Appl. No. 12/502,848, Final Office Action mailed Nov. 16, 2011, 12 pgs.
U.S. Appl. No. 12/502,848, Non Final Office Action mailed Jul. 14, 2011, 10 pgs.
U.S. Appl. No. 12/502,848, Notice of Allowance mailed Mar. 6, 2012, 5 pgs.
U.S. Appl. No. 12/502,848, Notice of Allowance mailed Jul. 9, 2012, 5 pgs.
U.S. Appl. No. 12/502,848, Response filed Feb. 14, 2012 to Final Office Action mailed Nov. 16, 2011, 12 pgs.
U.S. Appl. No. 12/502,848, Response filed Jun. 15, 2011 to Restriction Requirement mailed May 20, 2011, 3 pgs.
U.S. Appl. No. 12/502,848, Response filed Oct. 13, 2011 to Non Final Office Action mailed Jul. 14, 2011, 15 pgs.
U.S. Appl. No. 12/502,848, Restriction Requirement mailed May 20, 2011, 6 pgs.
U.S. Appl. No. 12/624,142, Notice of Allowance mailed May 31, 2011, 8 pgs.
U.S. Appl. No. 12/624,142, Notice of Allowance mailed Sep. 20, 2011, 7 pgs.
U.S. Appl. No. 12/624,142, Supplemental Notice of Allowability mailed Dec. 2, 2011, 2 pgs.
U.S. Appl. No. 13/674,591, Advisory Action mailed Jul. 15, 2015, 3 pgs.
U.S. Appl. No. 13/674,591, Examiner Interview Summary mailed Jan. 9, 2015, 3 pgs.
U.S. Appl. No. 13/674,591, Final Office Action mailed Mar. 3, 2015, 10 pgs.
U.S. Appl. No. 13/674,591, Final Office Action mailed Mar. 3, 2016, 10 pgs.
U.S. Appl. No. 13/674,591, Non Final Office Action mailed Sep. 29, 2015, 9 pgs.
U.S. Appl. No. 13/674,591, Non Final Office Action mailed Oct. 10, 2014, 9 pgs.
U.S. Appl. No. 13/674,591, Response filed Jan. 12, 2015 to Non Final Office Action mailed Oct. 10, 2014, 18 pgs.
U.S. Appl. No. 13/674,591, Response filed Jan. 29, 2016 to Non Final Office Action mailed Sep. 29, 2015, 19 pgs.
U.S. Appl. No. 13/674,591, Response filed Jul. 6, 2015 to Final Office Action mailed Mar. 3, 2015, 14 pgs.
U.S. Appl. No. 13/674,591, Response filed Sep. 12, 2014 to Restriction Requirement mailed Aug. 22, 2014, 2 pgs.
U.S. Appl. No. 13/674,591, Restriction Requirement mailed Aug. 22, 2014, 6 pgs.
European Application Serial No. 09760429.2, Decision to Grant mailed Dec. 11, 2014, 2 pgs.
European Application Serial No. 09760429.2, Office Action mailed Sep. 14, 2011, 2 pgs.
European Application Serial No. 09760429.2, Response filed Mar. 26, 2012 to Office Action mailed Sep. 14, 2011, 9 pgs.
International Application Serial No. PCT/US2010/041826, International Preliminary Report on Patentability mailed Jan. 26, 2012, 8 pgs.

MULTI-BEARING ACETABULAR PROSTHESIS

CROSS-REFERENCE TO RELATED APPLICATIONS

This application is a continuation of U.S. application Ser. No. 12/624,142 filed on Nov. 23, 2009, which claims the benefit of U.S. Provisional Application No. 61/117,249, filed on Nov. 24, 2008. The entire disclosures of the above applications are incorporated herein by reference.

FIELD

The present disclosure relates to a modular prosthesis, particularly to an acetabular prosthesis including a plurality of liners operable to interconnect with a single acetabular shell.

BACKGROUND

The statements in this section merely provide background information related to the present disclosure and may not constitute prior art.

Articulating regions of the anatomy can include areas where two bone sections move relative to one another. For example, an acetabulum can provide a region for articulation with a femoral head. The articulating region, however, can become injured or worn, but it can be replaced with various prostheses. Prostheses can replace the acetabulum, the femoral head, various other portions of the femur, or combinations thereof. The replacement of both the acetabulum and the femoral head is generally referred to as a total joint replacement.

The total joint replacement of the acetabulum and the femoral head requires a bearing or articulating surface for both the femoral head and the acetabulum. The articulating surfaces are generally positioned relative to the various portions of the remaining natural anatomy in a substantially fixed manner. Materials must be selected for the bearing surfaces for various purposes.

SUMMARY

A prosthesis to replace a portion of the anatomy, such as the acetabulum can include a first portion, such as a cup or shell, that can be fixed to, for example, the pelvis. The pelvis can be prepared in any appropriate manner to receive fixation of the cup. The prosthesis can include a second portion, such as a liner or bearing, that can be positioned relative to the shell to provide a bearing surface to articulate with a femoral head prosthesis. It will be understood, however, that a selected bearing component can be provided to articulate or provide a bearing surface relative to a natural femoral head.

The prosthesis system can include a single shell that can be interconnected with two or more bearing members. The bearing members can include various characteristics or material selections, such as a polymer bearing and a metal bearing. The polymer bearing can provide a relatively soft surface for a member to bear against. The metal bearing, relative to the polymer bearing, can provide a substantially hard or tough surface to bear against. The different bearing materials can also include different connection portions to interconnect with the shell. The shell can include connecting regions to connect with the multiple bearing members.

Further areas of applicability will become apparent from the description provided herein. It should be understood that the description and specific examples are intended for purposes of illustration only and are not intended to limit the scope of the present disclosure.

DRAWINGS

The drawings described herein are for illustration purposes only and are not intended to limit the scope of the present disclosure in any way.

DETAILED DESCRIPTION

The following description is merely exemplary in nature and is not intended to limit the present disclosure, application, or uses. Although various embodiments are discussed below, including exemplary materials, it will be understood that any appropriate materials or combinations may be selected for use with the assemblies.

Figure 1A:
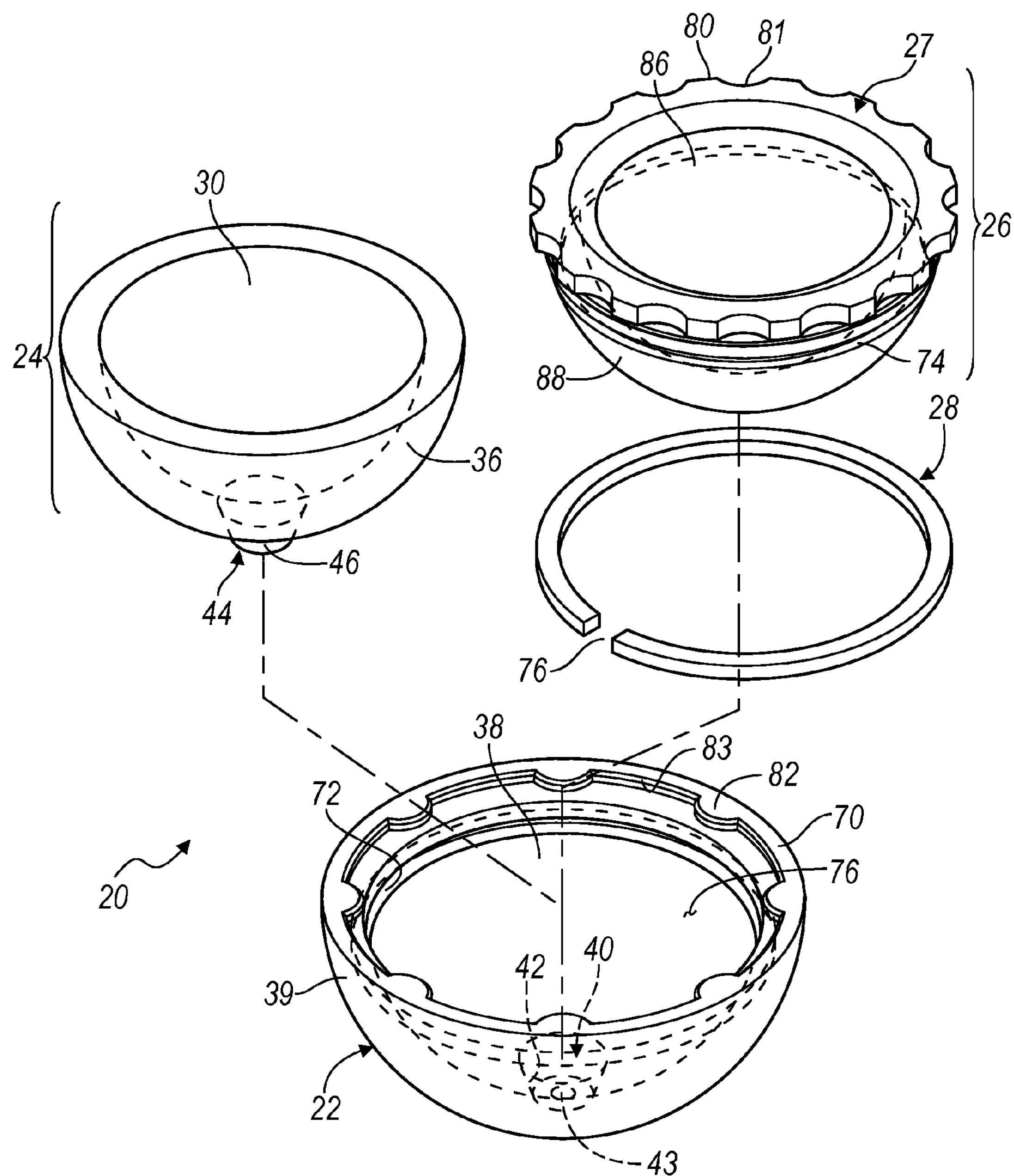
FIG. 1A is a perspective exploded view of an acetabular assembly, according to various embodiments.
Figure 7:
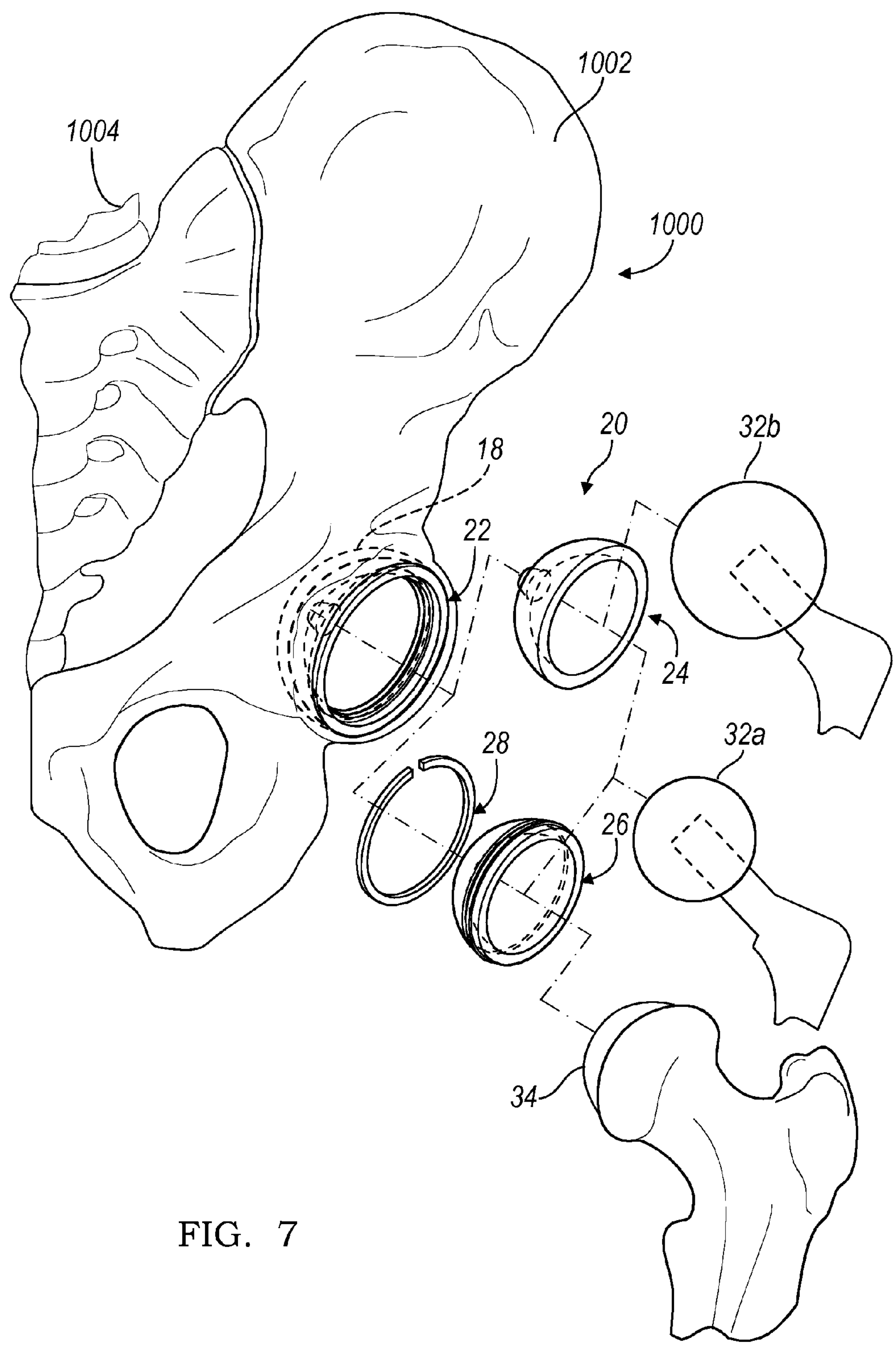
FIG. 7 is an environmental view of an acetabular assembly positioned relative to an acetabulum of a patient.

With reference to FIGS. 1A and 7, in a selected procedure, such as an implantation of an acetabular prosthesis implantation procedure, an acetabular prosthesis, according to various embodiments, can be positioned into an acetabulum 18. According to various embodiments, an acetabulum prosthesis assembly can include a multiple-bearing acetabular assembly 20 including a shell prosthesis 22 into which a first liner 24 and a second liner 26 can be positioned with or without a connecting member 28. The first liner 24 and the second liner 26 can be made of the same or different materials and different sizes, but can be provided to interconnect with the single shell 22, according to various embodiments.

Figure 1B:
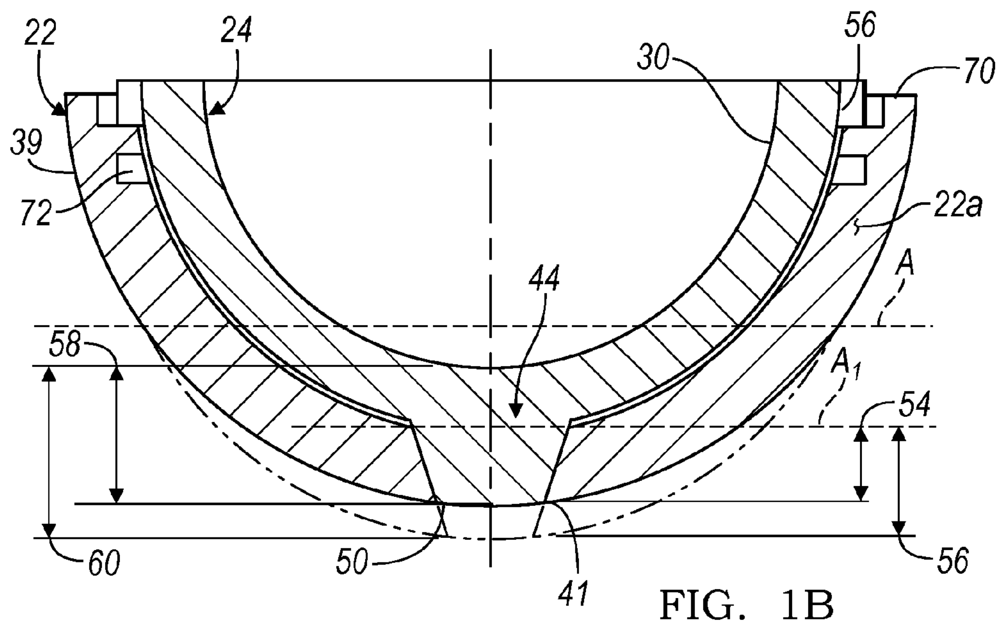
FIG. 1B is a cross-sectional view of a first liner positioned in a shell of the assembly of FIG. 1A, according to various embodiments.

The first liner 24 can be formed of a substantially or relatively hard or rigid material, such as a ceramic material (e.g. the ceramic Biolox® Delta sold by CeramTec, having a place of business in South Carolina), metals (e.g. titanium, titanium alloys, stainless steel alloys, cobalt chromium alloys), and other appropriate metals or rigid polymers, such as polyetheretherketone (PEEK), for example. The rigid material of the first liner 24 can be any appropriate biocompatible rigid material that can provide a bearing surface for a selected portion, such as a femoral head implant or a natural femoral head 34, as illustrated in FIG. 7. With reference to FIGS. 1A, 1B, and 7, the first liner 24 can include an internal bearing surface 30 that is operable to bear on or articulate with a femoral head implant 32*a*, 32*b* or a natural femoral head 34. The bearing surface 30 can be provided in any appropriate manner, such as a highly polished or substantially smooth surface for articulation with a selected member.

The first liner 24 can also include an exterior surface 36 which can be provided to cooperate with an interior surface 38 of the shell 22. The interior surface 38 of the shell 22 can define a void generally in an area between a line Al and the rim 70 of the shell 22. The void can include a generally concave shape depicted in various embodiments. The interior surface 38 of the shell 22 can be provided in any appropriate manner, such as substantially highly polished or substantially smooth. The interior surface 38 can contact the exterior surface 36 of the first liner 24 substantially tightly or with any appropriate gaps. For example, the interior surface 38 can be provided to not contact the exterior surface 36 to assist in providing a select interaction of tapers, as discussed herein. Alternatively, the interior surface 38 can contact the exterior surface completely or in part, according to various embodiments.

The first liner 24 can be interconnected or fixedly positioned relative to the shell 22 via the interconnection of a female taper 40 defined substantially near a center and/or apex of the shell 22. The female taper 40 can be defined by a female taper wall 42. The female taper wall 42 can define part of or be positioned near an apical hole or passage 43. The taper wall 42 can be formed in the shell 22 in any appropriate manner, such as casting, machining, etching, etc. The female wall taper 42 can also be provided in any appropriate configuration such as substantially smooth or rough for connection with a male taper 44 defined by the first liner 24.

The male taper 44 can be formed substantially integrally or as a single portion with the first liner 24 and defined by a male taper wall 46. The male taper 44 need not be a separate portion that is interconnected with the exterior surface 36 of the first liner 24, but can define a portion of the exterior surface of the first liner 24. The male taper wall 46 can include an appropriate angle relative to a central or concentric axis of the first liner 24.

The angle of the male taper wall 46 can be substantially identical or similar to an angle of the female taper wall 42. The tapers 40, 44 can include selected angles such as about 1 degree to about 45 degrees. The angles can allow the male taper 44 to engage the female taper 40 in a substantially locked or connected manner, such as with a Morse taper. The interconnection of the tapers 40, 44 can allow a fixation of the first liner 24 into the shell 22 at a selected time.

The female taper 40 can also assist in aligning the first liner 24 during implantation of the first liner 24 into the shell 22. Furthermore, the female taper 40 can be positioned near the throughbore or passage 43 to assist with implantation of the shell 22. The passage 43 can be used with an implantation tool to assist in positioning the shell 22 in a selected location. Also, an apical plug or other member can be positioned in the apical hole 43, if selected. The shell 22, according to various embodiments, can also include other bores, external projections, etc., to assist in positioning and fixing the shell 22 to the anatomy 500. Exemplary implantation tool systems include apical hole inserters, sold by Biomet, Inc. of Warsaw, Ind., USA.

The shell 22 can also be provided in different sizes or configurations. For example, a diameter or height of the shell 22 can be altered based upon different portions that articulate with the first liner 24, the size of the patient, or other appropriate considerations. The shell 22 defined by a shell wall portion or member 22*a* can also be provided in multiple thicknesses.

A first thickness 54 can be provided which can be less than a second thickness 56. The first and second thicknesses 54, 56 can also alter or change the dimensions of the female taper 40. The male taper 44 can likewise include a first thickness 58 or a second thickness 60. The first and second thicknesses 58, 60 of the male taper 44 can be formed to be substantially complementary or operably complement the female taper thicknesses 54, 56. It will be understood, however, that a system or kit of the shells 22 and the first liners 24 can include multiple liners of multiple sizes, including two or more thicknesses of the female taper 40 or the male taper 44.

Different sizes can be provided for different reasons. For example, the different sizes of the shell 22 with different sizes of the first liner 24 can include different thicknesses that require different thicknesses of the female and male tapers 40, 44. The thickness of the tapers 40, 44 can be selected for specific or selected applications. For example, a thicker taper, such as the thicker female taper 56 and the thicker male taper 60, can be provided for a substantially stronger or longer wear connection. A thicker taper can be provided in a substantially younger or more active patient. Other reasons may also exist for using different thicknesses. For example, if a patient has a deeper or substantially worn acetabulum, a deeper or thicker taper may fit better in that patient.

As is clearly illustrated in FIGS. 1A and 1B, the female taper 40 defined by the shell 22 can be positioned at a location of the shell 22 that is substantially a distance away, such as a maximum distance away, from a rim 70 of the shell 22. The rim 70 generally defines a portion of an exterior surface of the shell 22. Positioned near the rim 70 can be a groove or connection area 72. The first groove 72 can receive or interconnect with the connecting member 28. The connecting member 28 can cooperate with a second groove 74 of the second liner 26 to assist in interconnecting the second liner 26 with the shell 22. The first groove 72 defined by the shell 22 can be positioned substantially near the rim 70 of the shell 22. This can position the first groove 72 at a distance from the apical hole or passage 43. The grooves 72, 74 can be sized in any appropriate manner to receive or cooperate with the connecting member 28, such as in the Ringlac® acetabular implant sold by Biomet, Inc. of Warsaw, Ind., USA.

Figure 1C:
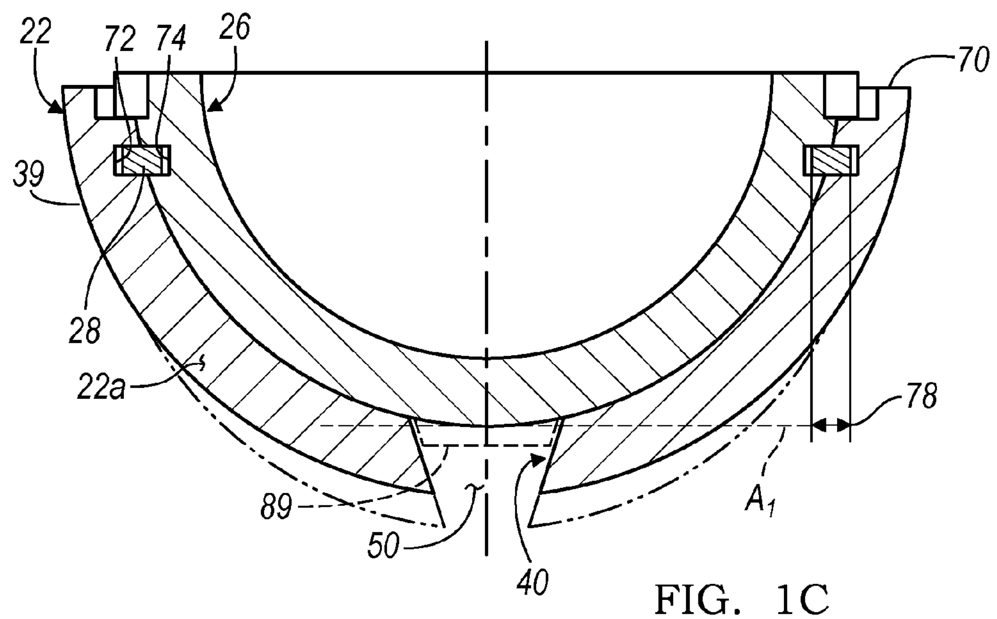
FIG. 1C is a cross-sectional view of a second liner positioned in a shell of the assembly of FIG. 1A, according to various embodiments.

The second liner 26 can be formed of any appropriate materials, such as polymers including ultra-high molecular weight polyethylene (UHMWPE) or polyetheretherketone (PEEK). Any appropriate material can be used to form the second liner 26, but the second liner 26 may generally be substantially softer or less rigid than the first liner 24. Continuing to refer to FIG. 1A and additionally to FIG. 1C, the second liner 26 can interconnect or be positioned relative to the shell 22 with the connecting member 28. The second liner 26, the connecting member 28, and the shell 22 can be provided as three separate pieces or the connecting member 28 can be pre-fit into either of the grooves 72, 74 defined by the second liner 26 or shell 22. This can allow a user, such as a surgeon, to press the second liner 26 into the shell 22 and the connecting member 28 can compress or expand relative to the opening or void 76 to allow it to pass over a portion of the shell 22 or the second liner 26 and expand into the grooves 72, 74. The connecting member 28 includes a width 78 great enough to engage both the first groove 72 and the second groove 74 in the respective shell 22 and the second liner 26. Therefore, the connecting member 28 can fixedly hold the second liner 26 relative to the shell 22, at least in an axial position.

The second liner 26 can also include an anti-rotation system including an anti-rotation tab 80 and associated depression 81 at an upper rim 27 of the second liner 26. The rim 70 of the shell 22 can also include complementary anti-rotation projections 82 and associated depressions 83 to assist in minimizing or eliminating rotation of the second liner 26 relative to the shell 22 after implantation. The anti-rotation projections 82 can be positioned exterior to the internal surface or cavity 38 of the shell 22.

The second liner 26 can also include any appropriate size for positioning in the shell 22. The second liner 26 can be selected to include an articulation or internal surface 86 for articulation relative to the femoral implant 32*a*, 32*b* or a natural femoral head 34. An external surface 88 of the second liner 26 can also engage the internal surface 38 of the shell 22 in an appropriate manner, such as a substantially fixed or non-moving manner.

The second liner 26 can also include an optional projection 89. The projection 89 can extend from the exterior surface 88 of the second liner 26 and be positioned in or engage the female taper 40. According to various embodiments, the projection 89 does not lock with the female taper 40. The projection 89 can be provided, according to various embodiments, only for alignment of the second liner 26. Alternatively, the projection 89 may lock with the female taper 40.

Briefly, the provision of the first liner 24 and the second liner 26 allows for a pre-operative or intra-operative selection of liners for positioning within the shell 22. In addition, or alternatively, the provision of the first liner 24 and the second liner 26 that can engage the shell 22 can minimize the number of parts for a procedure. For example, rather than requiring a first shell to engage the first liner 24 and a second shell to engage the second liner 26, only the single shell 22 is needed to engage both the first liner 24 and the second liner 26.

Figure 2A:
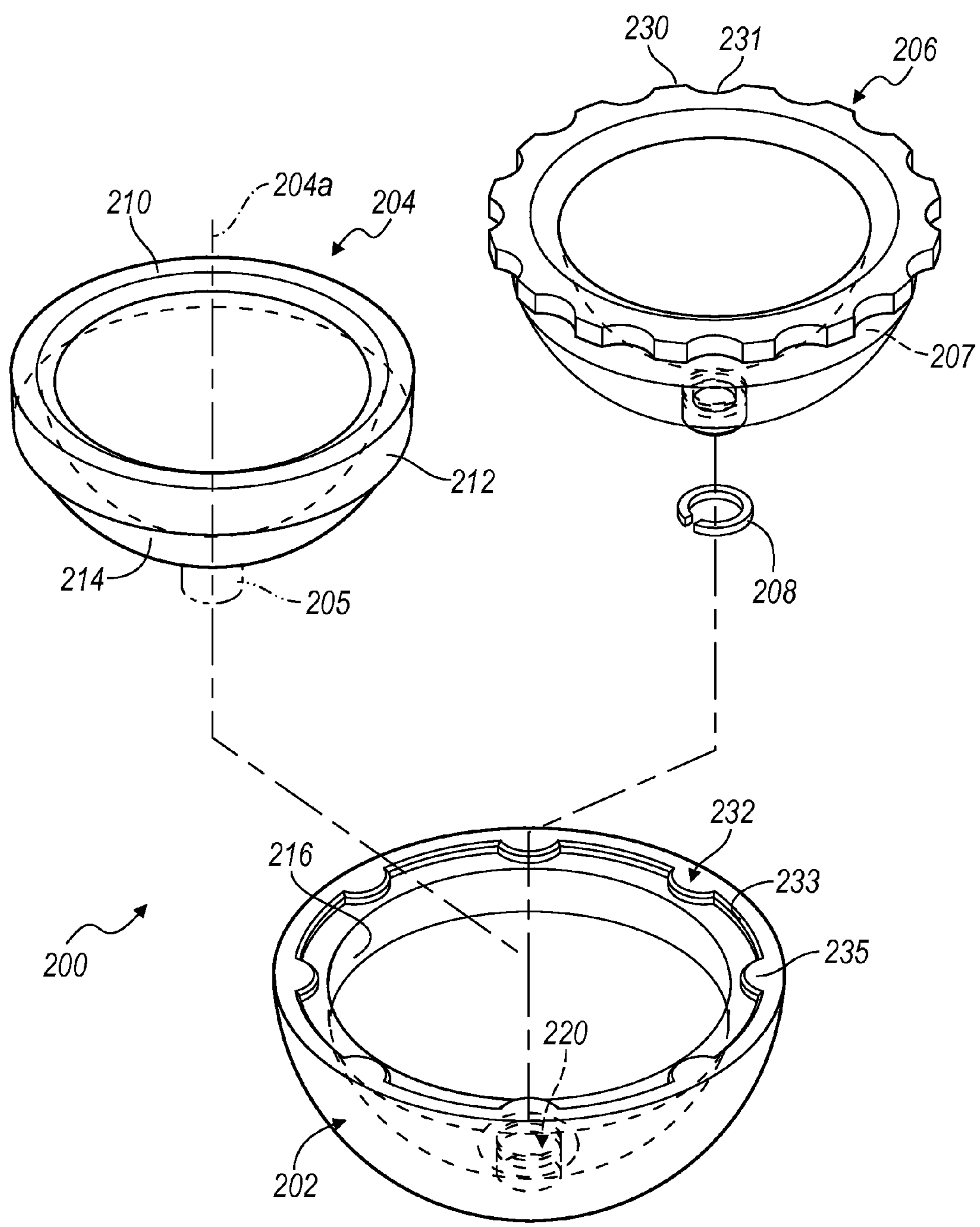
FIG. 2A is a perspective exploded view of an acetabular assembly, according to various embodiments.
Figure 2B:
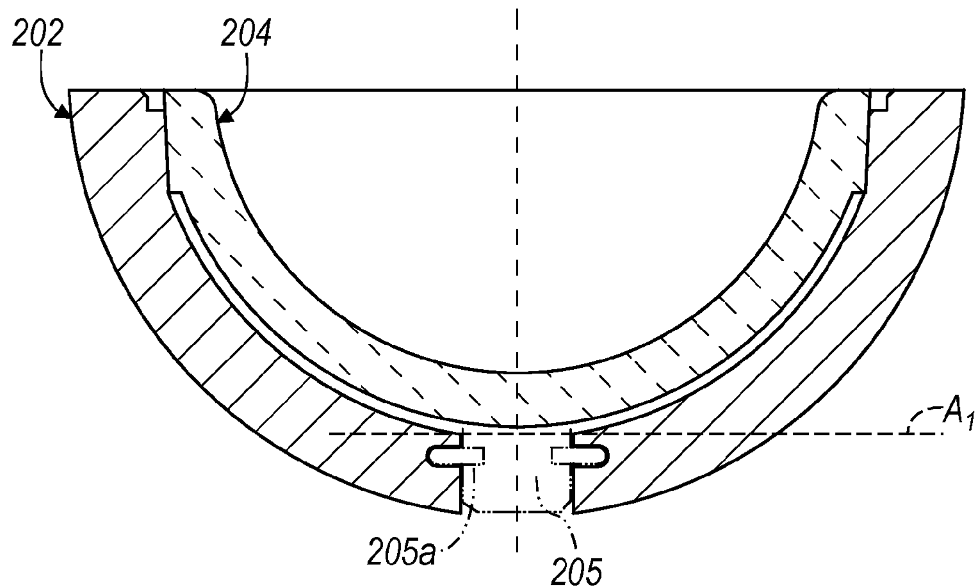
FIG. 2B is a cross-sectional view of a first liner positioned in a shell of the assembly of FIG. 2A, according to various embodiments.
Figure 2C:
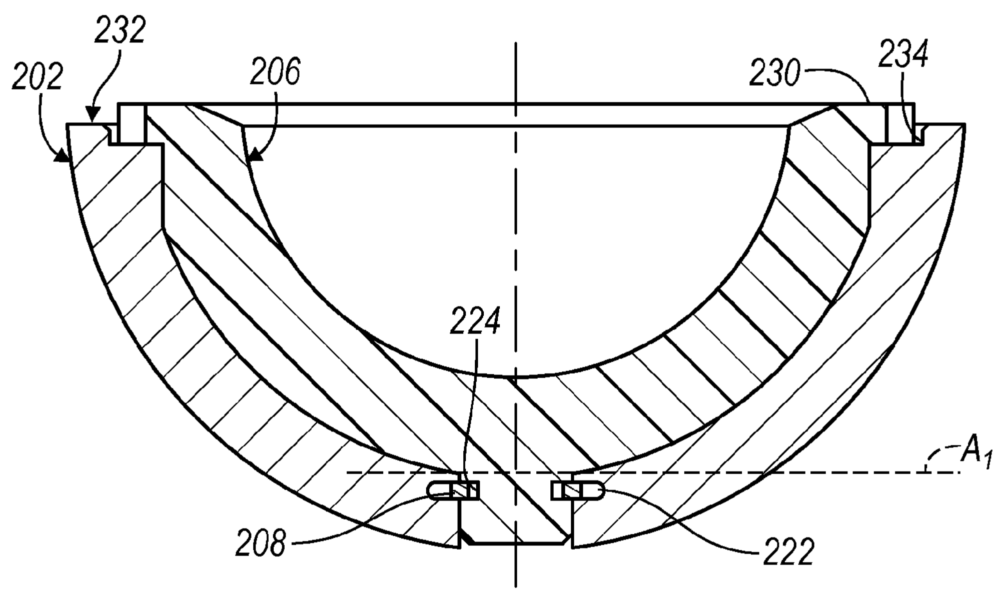
FIG. 2C is a cross-sectional view of a second liner positioned in a shell of the assembly of FIG. 2A, according to various embodiments.

According to various embodiments, a multiple-liner acetabular prosthesis assembly 200 is illustrated in FIGS. 2A-2C. The acetabular prosthesis assembly 200 can include a single shell 202 that can be interconnected with a first bearing or liner 204. The first liner 204 can be formed of a substantially hard or rigid material, including ceramic or metal alloys, similar to the first liner 24 discussed above. A second liner 206 can include or be interconnected with a shell 202 with a connecting member 208. The second liner 206 can be formed of a less rigid or softer material, including the polymers discussed above in relation to the second liner 26. The first liner 204 or the second liner 206 can be interconnected with the single shell 202, similar to the provision of the first liner 24 and the second liner 26 that can also be interconnected with the single shell 22. The first liner 204 and the second liner 206, however, can include different connection portions for interconnecting with the single shell 202.

The first liner 204 can include a rim 210 defined at an exterior edge of the liner 204. Positioned below the rim 210 of the first liner 204 is a taper wall 212 that defines a substantially straight wall portion relative to an exterior wall 214 of the remainder of the first liner 204.

The straight wall portion of the taper wall 212 can include a taper relative to a substantially central or concentric axis 204*a* defined by the first liner 204. The taper angle of the taper wall 212 can be any appropriate taper angle, including those that are similar to the angles of the taper wall 46. For example, the taper connection can define a Morse taper with a female or internal taper 216 defined by the shell 202. The tapers 212, 216 can be provided substantially complementary or mating such that the two tapers 212, 216 can be used to lock the first liner 204 relative to the shell 202. The substantially rigid material of the first liner 204 can be used to ensure a rigid connection of the two tapers 212, 216.

As discussed above, the first liner 204 can be positioned into the shell 202 and fixed in place by positioning the two tapers 212, 216 relative to one another. The taper connection can offer a substantially fixed position of the first liner 204 in both an axial position and rotational position relative to the shell 202. Also, the tapers 212, 216 can include any appropriate heights or dimensions. Further, the first liner 204 can include a plurality of liners each measuring different heights to allow selection of an amount of contact area between the male taper 212 and the female taper 216. Each of a plurality of the first liners 204 can also include different dimensions, such as an internal diameter, an external diameter, etc.

The shell 202 can also include an apical or proximal bore or opening 220. The opening 220 in the shell 202 can be used similarly to the apical hole 43 in the shell 22. For example, an implantation instrument can be used to engage the opening 220 to implant the shell 202 relative to the acetabulum 18. Further, the opening 220 can include an internal or first groove 222 that can engage or receive the connecting member 208. The second shell 206 can include a second groove 224 to also partially or completely receive or engage the connecting member 208. Similar to the connecting member 28, the connecting member 208 can include a recess or opening to allow for a deformation of the connecting member 208. Therefore, as a user, such as a surgeon, presses the second liner 206 into the opening 220, the connecting member 208 can first compress and then rebound to engage both the first groove 222 and the second groove 224 to substantially hold the second liner 206 axially relative to the shell 202. Alternatively, the connecting member 208 can also first be positioned in the first groove 222 or placed between the liner 206 and shell 202 prior to a surgeon or other user pressing the liner 206 into the shell 202.

The second liner 206 can also include an anti-rotation system including anti-rotation projections 230 and recesses 231. The shell 202 at a rim or upper portion 232 can include a complementary anti-rotation system including recesses 233 and projections 235. The anti-rotation system can resist rotation of the second liner 206 . The second liner 206 can also be held axially in the shell 202 with the locking system discussed above.

The second liner 206 can also be formed in differing dimensions, for example, thicknesses and diameters, to be interconnected with the shell 202. The second liner 206 can be provided in differing sizes for reasons similar to those disclosed above, including patient's specifications, implant selections, and the like. Also, a kit of a plurality of the first liners 204 and second liners 206 can be provided with varying characteristics.

Nevertheless, according to various embodiments, the shell 202 can provide for a connection between different liners, such as the first liner 204 and the second liner 206. The connection areas defined by the shell 202 can be provided at substantially distant or extremely distant positions relative to each other. The female taper 216 can be positioned substantially near the rim 232 while the groove 222 can be positioned substantially near or in the apical opening 220. Therefore, the two connection systems can be provided substantially independent of one another, but still allowing for interconnection of multiple connecting portions. The two connection systems, however, can also be provided to both engage and connect to a single liner, as discussed herein. In addition, for reasons similar to the acetabular system 20, the multiple bearings can be interconnected with a single shell 202 for various reasons.

Figure 3A:
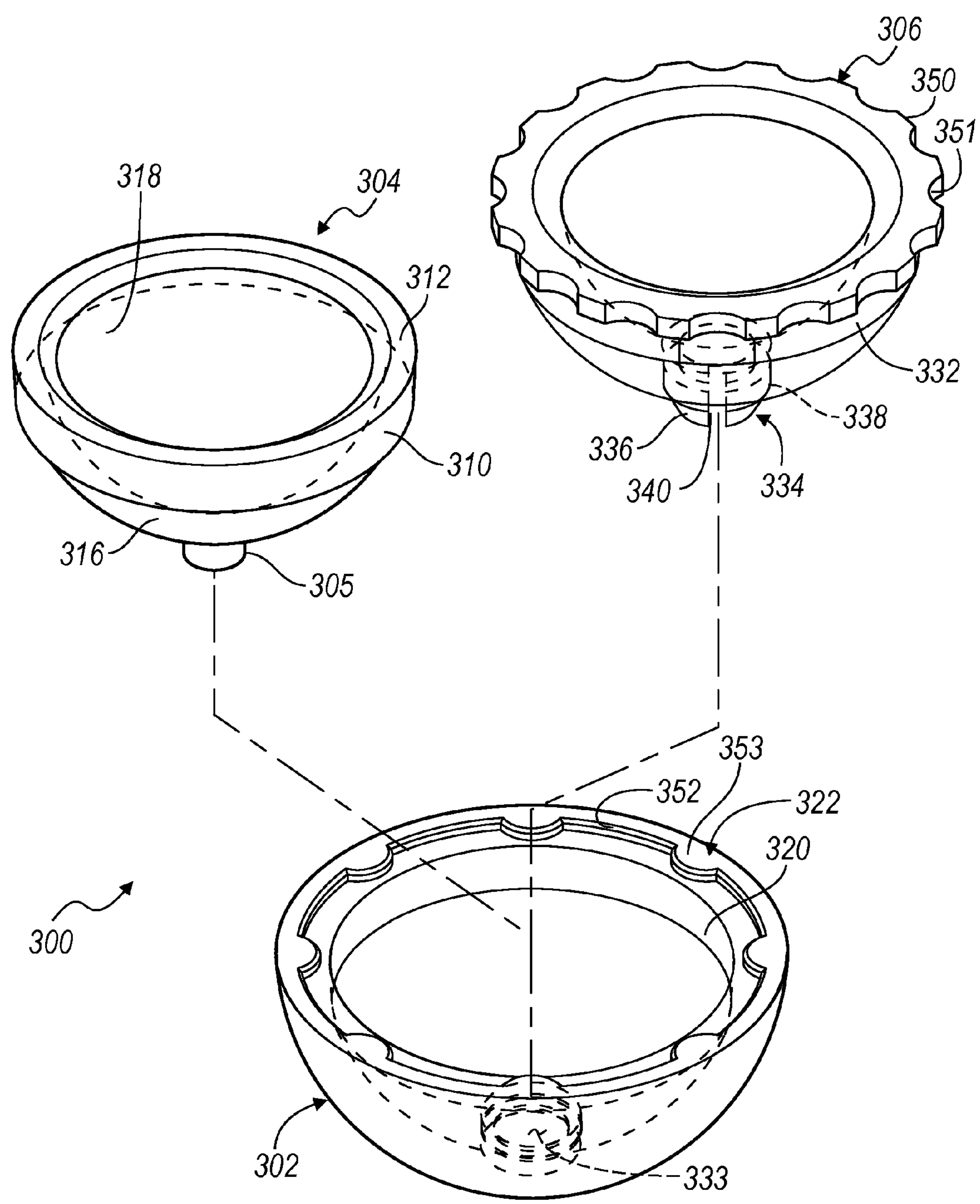
FIG. 3A is a perspective exploded view of an acetabular assembly, according to various embodiments.
Figure 3B:
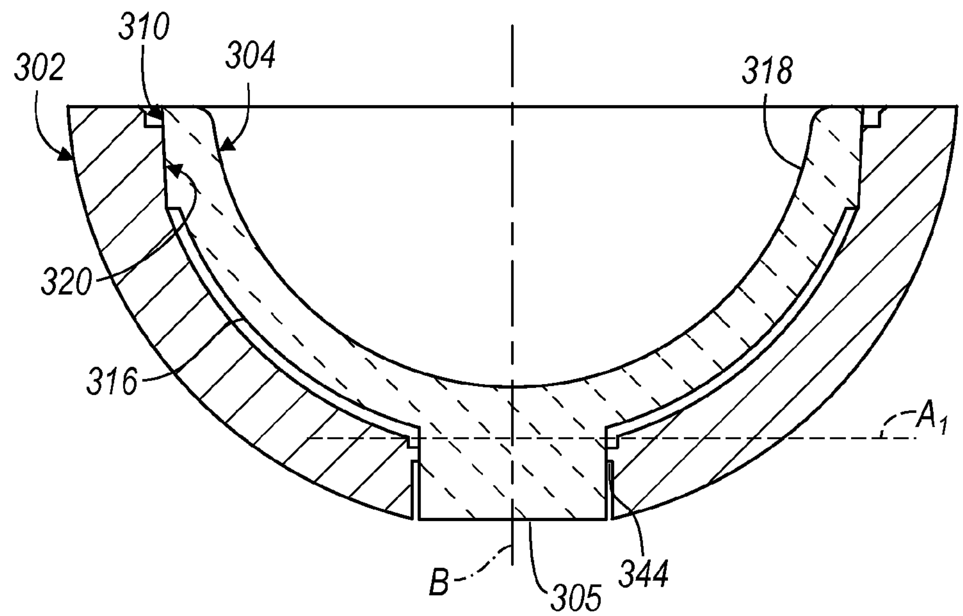
FIG. 3B is a cross-sectional view of a first liner positioned in a shell of the assembly of FIG. 3A, according to various embodiments.
Figure 3C:
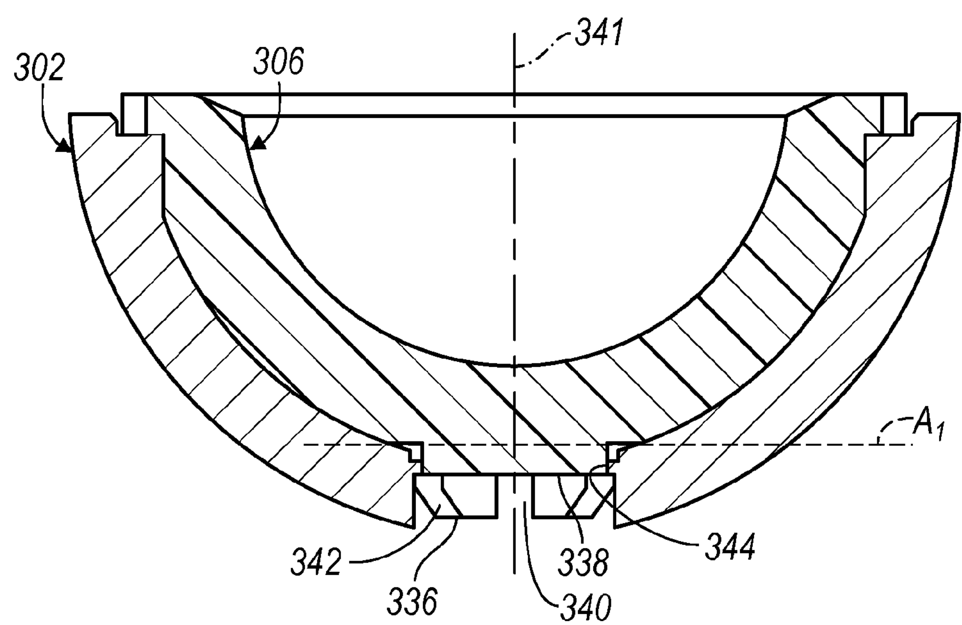
FIG. 3C is a cross-sectional view of a second liner positioned in a shell similar to the assembly of FIG. 3A, according to various embodiments.

With reference to FIGS. 3A-3C, a multiple liner acetabular system 300, according to various embodiments, is illustrated. The acetabular assembly 300 can include a single shell 302, a first liner or bearing member 304 and a second liner or bearing member 306. The shell 302 can be interconnected with the liners 304, 306.

Briefly, the first liner 304 can be substantially similar to the first liner 204 of the acetabular assembly 200. The first liner 304 can include a male taper portion 310 at or near a rim 312 of the first liner 304. An exterior portion 316 of the first liner 304 can be provided to engage or be positioned within the shell 302 in any appropriate manner. An internal surface 318 of the first liner 304 can be provided to articulate with any appropriate portion, such as a femoral implant 32*a*, 32*b* or a femoral head 34. In addition, similar to the shell 202 of the acetabular assembly 200, the shell 302 includes a female taper 320 at or near a rim 322 of the shell 302. The female taper 320 can be provided to substantially mate with or be complementary to the male taper 310 defined by the exterior of the first liner 304. As discussed above, the tapers 310, 320 can be substantially complementary and of any appropriate angle. For example, the tapers 310, 320 can be formed to allow or form a Morse taper connection between the two tapers 310, 320. The Morse taper connection, or similar taper connection, can allow the first liner 304 to be substantially locked or fixed relative to the shell 302. The taper fixation can allow both axial and rotational fixation of the first liner 304 relative to the shell 302.

The second liner 306 can also be similar to the second liner 206 of the acetabular assembly 200. The second liner 306 can be formed of a material that is softer than the first liner 304, such as a polymer. The second liner 306 can also include an interior surface 330 for articulation with a selected portion or component, such as a femoral head implant 32*a*, 32*b* or a natural femoral head 34. An exterior surface 332 of the second liner 306 can also be provided to engage the shell 302 in a selected manner, such as in a contacting fit.

As illustrated in FIGS. 3A and 3B, a nipple or projection 305 can extend from the exterior wall 316 of the first liner 304 to be positioned relative to an opening 333 in the shell 302. It will be understood that the projection 305 can be substantially cylindrical and need not engage any portion of the shell 302 once the first liner 304 is positioned within the shell 302. For example, the projection 305 can assist in aligning the first liner 304 with the shell 302 to ensure that the respective tapers 310, 320 are aligned for proper engagement and fixation of the first liner 304 within the shell 302. Once the first liner 304 is engaged within the shell 302, the projection 305 need not engage or contact any portion of the shell 302. It will be understood, however, that the projection 305 can be configured to engage the shell 302 in any appropriate manner at any appropriate time, such as after interconnection of the first liner 304 with the shell 302. It will be further understood, that an alignment projection, such as the alignment projection 305, can be provided with any appropriate liner portion to assist in aligning the liner portion with the shell, such as the liners 24 and 204.

With reference to FIG. 3C, substantially near an apex or an end of the second liner 306 can be a gripping or connecting region 334. The gripping region 334 can include one or more flexible fingers 336 that are hingedly connected with a portion of the exterior of the second liner 306 via a hinge 338. The finger 336 can be allowed to flex, such as via an opening or void 340. The void 340 can allow the fingers 336 to deflect radially relative to a central axis 341 of the second liner 306. As illustrated in FIGS. 3A and 3C, the fingers 336 can deflect as the second liner 306 is positioned within the shell 302 and the fingers 336 can then rebound. A ledge or connecting portion 342 of the finger 336 can engage a ledge or connecting ring 344 defined by the shell 302. The connecting ring 344 of the shell 302 can be positioned substantially in or near the apical hole 333 or apex of the shell 332. The apical hole 333 can be provided for various other purposes, such as those discussed above including implantation or positioning of the shell 302 relative to the acetabulum 18.

The engagement of the finger 336 relative to the connecting member or ring 344 can substantially axially hold the second liner 306 relative to the shell 302. In addition, the second liner 306 can define fingers or projections 350 and respective depressions 351 that can engage or cooperate with recesses 352 and respective projections 353 of the shell 302 to substantially eliminate or reduce rotational movement of the second liner 306 relative to the shell 302. Thus, the second liner 306 can be resist rotation relative to the shell 302.

Figure 3D:
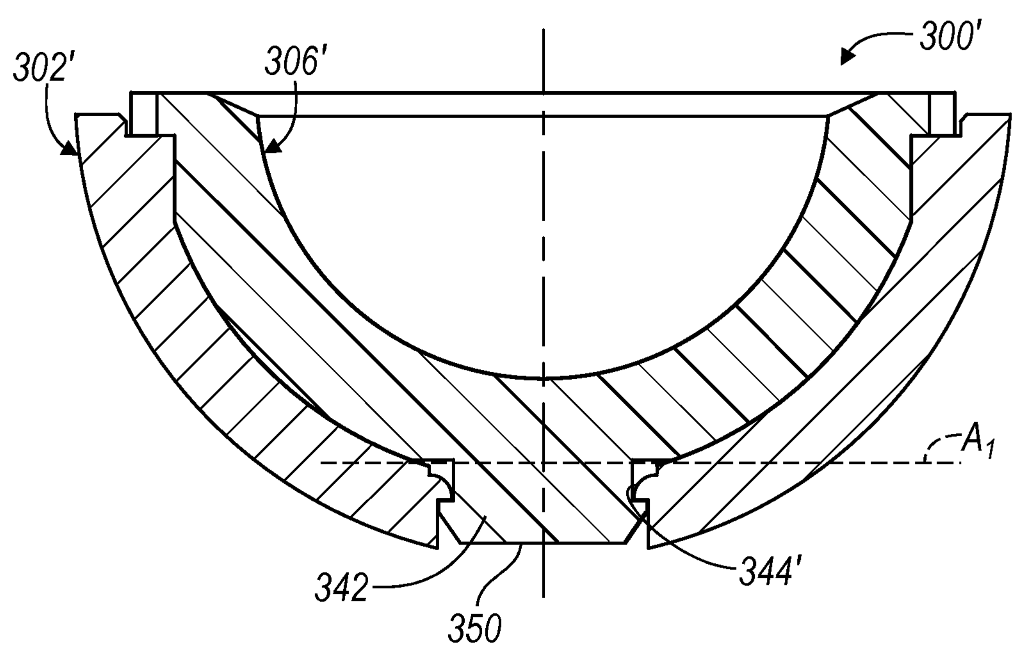
FIG. 3D is a cross-sectional view of a second liner positioned in a shell of the assembly of FIG. 3A, according to various embodiments.

With continuing reference to FIGS. 3A-3C, and additional reference to FIG. 3D, according to various embodiments, an acetabular assembly 300' can include an alternative shell 302' and an alternative liner 306'. The alternative liner 306' can be substantially similar to the second liner 306 except that a projection or nipple member 350 can extend from an exterior portion of the alternative liner 306' which includes a connecting portion 342' to engage a connecting ring or ledge 344'. The connecting ledge 344' can be a radially inwardly extending flange. The projecting portion 350 can be a substantially solid member. Insertion of the alternative liner 306' into the shell 302' can be accomplished by pressing the alternative liner 306' into the shell 302'. By applying a force into the alternative liner 306', the connecting portion 342' can compress or deflect enough to pass the connecting ring 344' to allow the alternative liner 306' to be connected to the shell 302'. This can be assisted, at least in part, by an upper curved or slanted surface of the connecting ring 344'. Accordingly, the projecting member 350 can be a substantially solid member to fixedly engage the shell 302'.

Figure 4A:
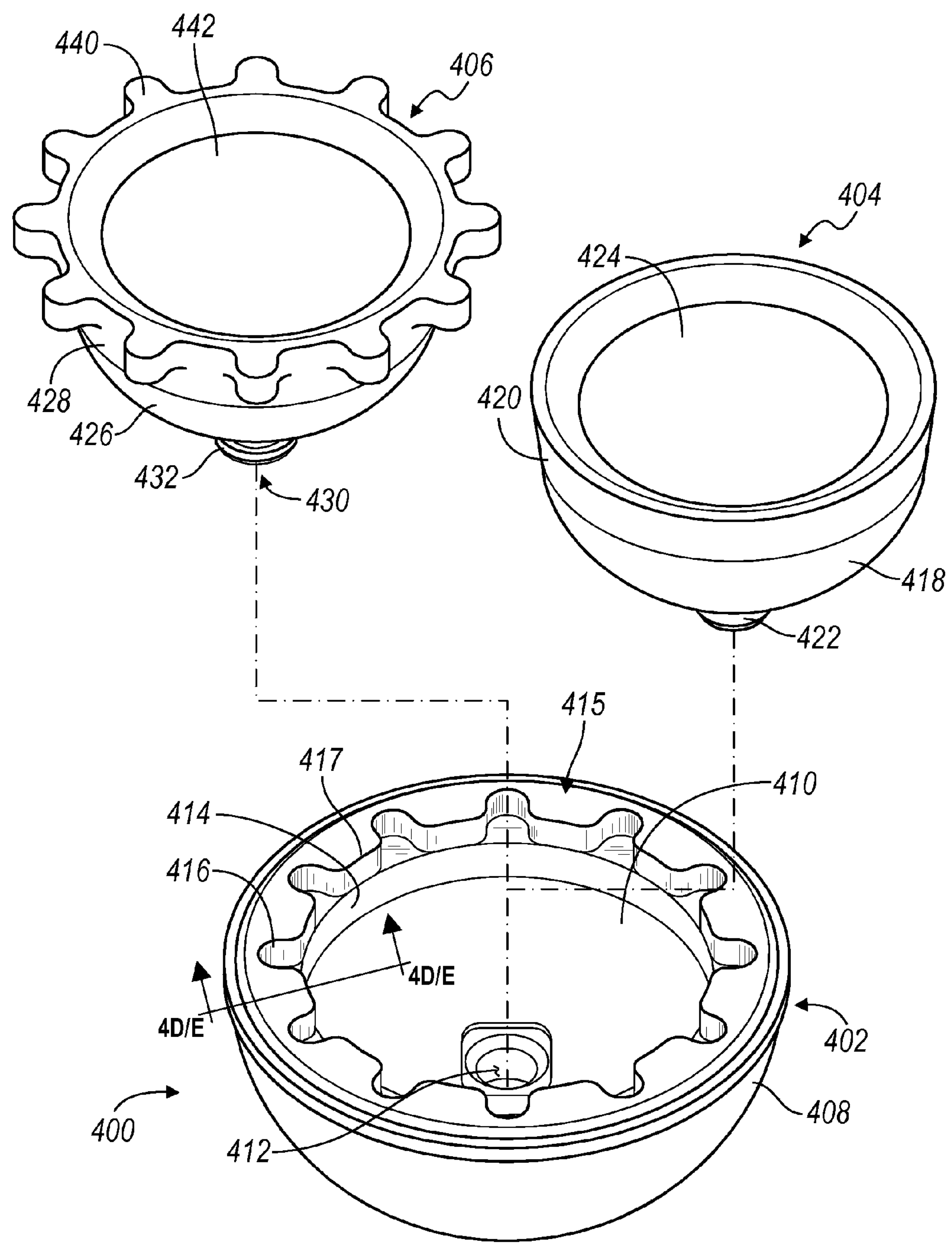
FIG. 4A is a perspective exploded view of an acetabular assembly, according to various embodiments.

With reference to FIG. 4A, an acetabular assembly 400, according to various embodiments, includes a shell 402 relative to which a first liner 404 or a second liner 406 can be positioned. The shell 402 can include an exterior wall 408 operable to contact various portions, such as an acetabulum of a patient. The exterior wall 408 can be substantially spherical or curved. The shell 402 can also include an interior wall 410. The interior wall 410 can be substantially spherical or curved. The interior wall 410 can also include a distal or apical hole 412 and a proximal or taper wall 414 that can define a selected angle or taper. The apical hole 412, or a portion positioned relative thereto, can be provided to engage an apical nipple or engagement portion as discussed herein. The taper wall 414 can be provided to engage a complementary taper wall of the selected liner 404, 406 as also discussed further herein. A rim 415 can define one or more anti-rotation detents 416 and projections 417. The detents 416 can be spaced around the rim 415 of the shell 402 to engage an anti-rotation system of a selected liner portion, as discussed further herein.

The first liner 404 can be provided to engage a portion of the interior wall 410 of the shell 402. For example, a first exterior wall portion 418 of the first liner 404 can engage a substantially hemispherical or semispherical inner wall 410 of the shell 402. The first liner 404 can also include an engagement or male taper 420 that is operable to engage the internal taper region 414 of the shell 402. The taper walls can provide a Morse or locking taper connection. For example, the angle of the taper wall 414, 420 can be about 1 degree to about 45 degrees.

The first liner 404 can be formed of a substantially rigid material, such as a ceramic material or metal, so that the male taper wall 420 is operable to engage the interior taper wall 414 in a substantially locking manner. An alignment or engagement nipple 422 can also be provided to assist in aligning of the first liner 404 relative to the shell 402 or for interconnecting the first liner 404 with the shell 402. It will be understood that the engagement of the taper wall 420 with the interior taper wall 414 can assist in substantially holding the first liner 404 relative to the shell 402 in both axial and rotational motion. The first liner 404 can also include an interior articulating wall 424 operable to articulate with a selected member, such as a natural femoral head 34 or a prosthetic femoral implant 32*a*, 32*b*, as discussed further herein.

Figure 4B:
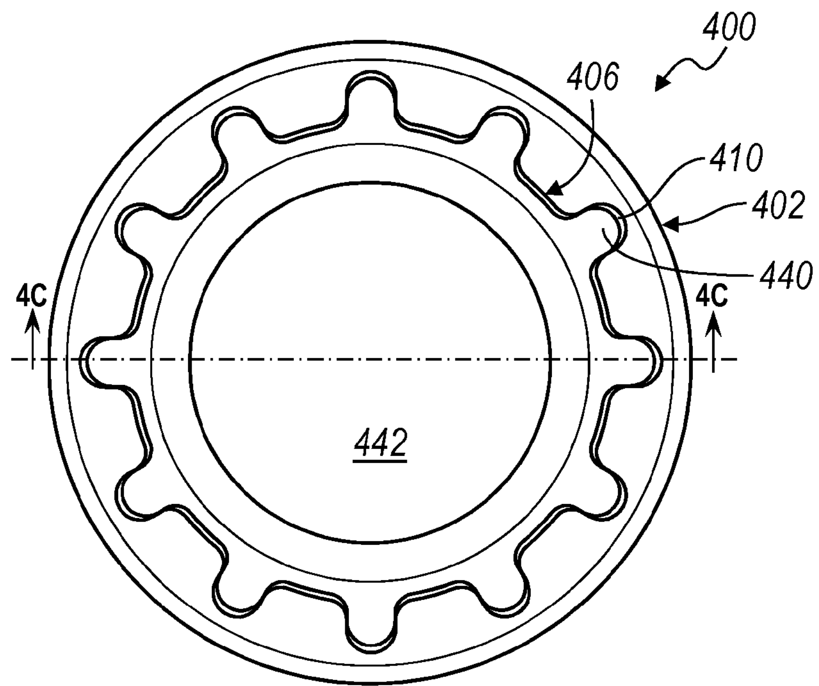
FIG. 4B is a top plan view of a liner inserted in a shell according to various embodiments.
Figure 4C:
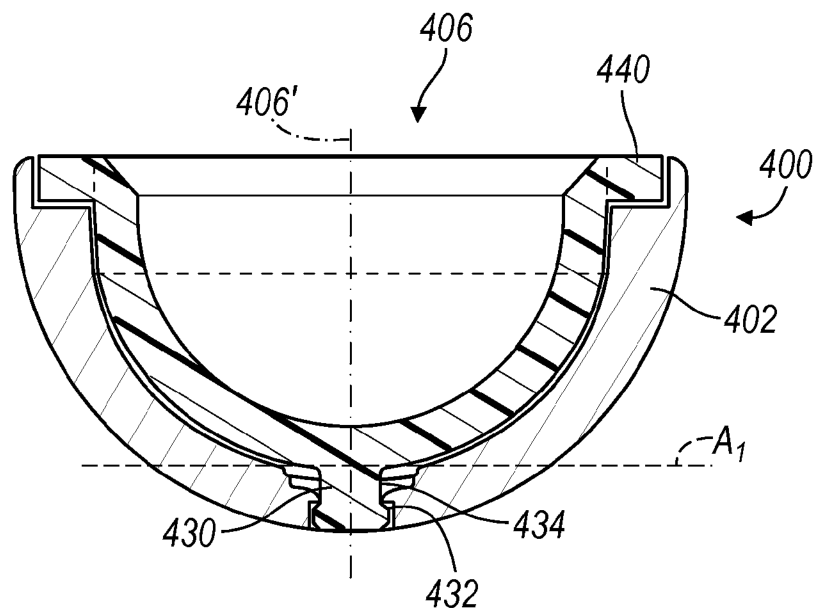
FIG. 4C is a cross-sectional view of a first liner positioned in a shell of the assembly of FIG. 4A, according to various embodiments.

With continuing reference to FIG. 4A and further reference to FIGS. 4B and 4C, the second liner 406 can also be positioned relative to the shell 402. The second liner 406 can be formed of an appropriate material, such as a moldable material including ultra-high molecular weight polyethylene or PEEK. The second liner 406 can include various portions, such as a first outer wall portion 426 operable to engage the first interior wall portion 410 of the shell 402 and a second exterior wall portion 428 operable to engage the interior taper wall 414 of the shell 402. In addition, a locking nipple or portion 430 can be provided to engage the apical hole 412 of the shell 402.

As specifically illustrated in FIG. 4C, the nipple 430 can include an engaging or extending portion 432 that is operable to pass a locking or shell ledge portion 434 to assist in holding or locking the second liner 406 relative to the shell 402. The locking nipple 430 can assist in holding the second liner 406 against axial motion relative to the shell 402. The second liner 406 can also include anti-rotation projections 440 and associated detents 441, which can cooperate with the detents 416 and projections 417 to assist in substantially eliminating or reducing rotational motion of the second liner 406 relative to the shell 402. The shell 402 can also include an interior wall 442 that can articulate with various portions, such as a natural femoral head or a femoral prosthesis.

Figure 4D:
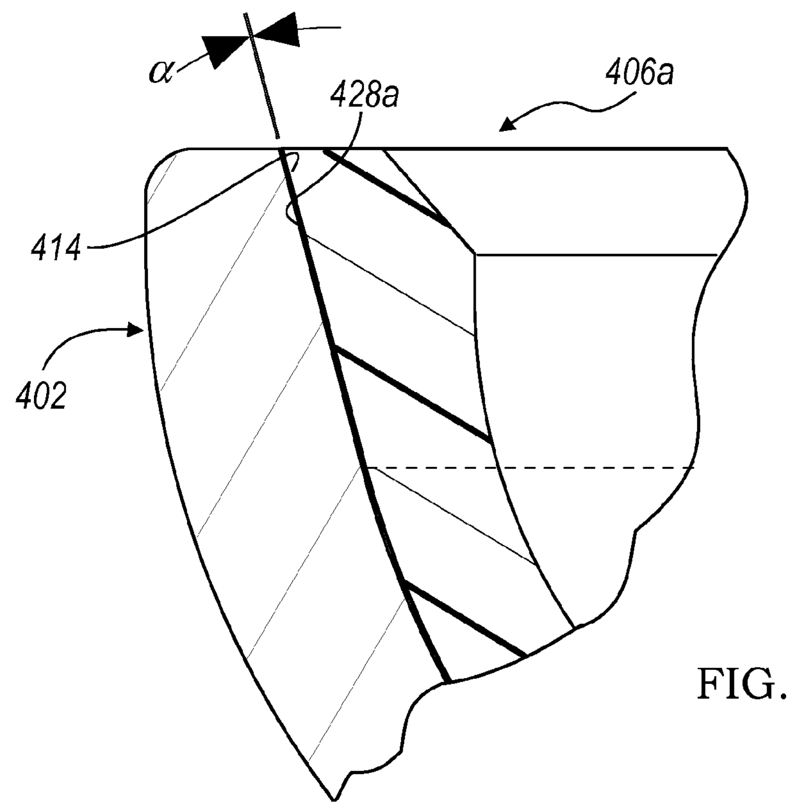
FIG. 4D is a detailed view of a liner and shell, according to various embodiments.
Figure 4E:
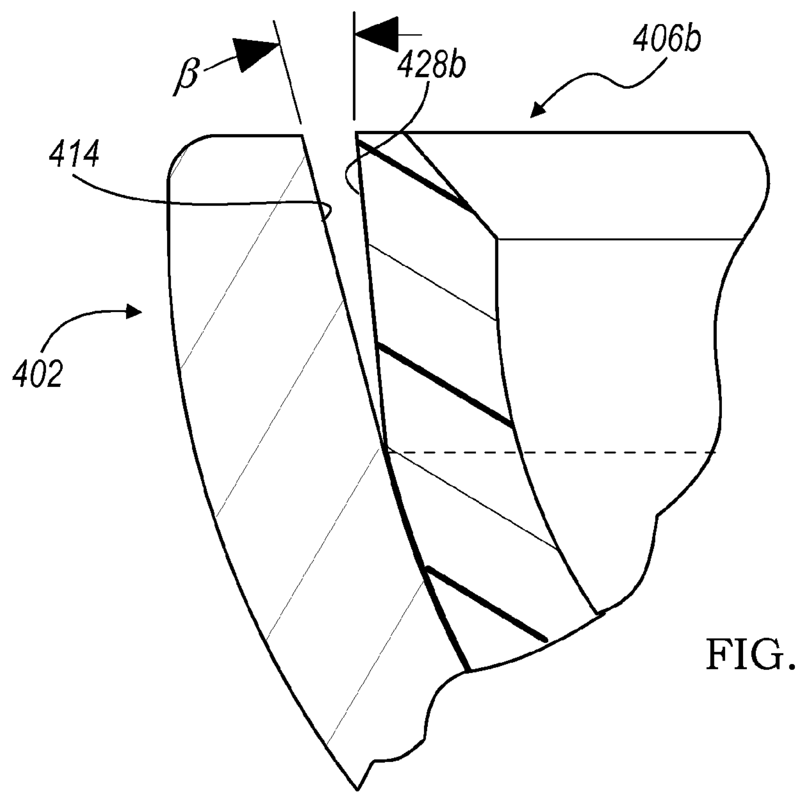
FIG. 4E is a detailed view of a liner and shell, according to various embodiments.

The second liner 406 can be provided substantially similar to the liners discussed above, such as the second liner 26 illustrated in FIG. 1A. According to various embodiments, however, the second exterior wall portion 428 of the second liner 406 can be provided relative to the internal taper wall 414 of the shell 402 according to various embodiments. For example, with reference to FIG. 4D, a liner 406*a*, substantially similar to the second liner 406, can be provided relative to the shell 402 including the internal taper wall 414 that includes a second wall portion 428*a*. The second wall portion 428*a* can be provided substantially parallel to the interior taper wall 414 of the shell 402. Accordingly, an angle $\alpha$ between the interior taper wall 414 of the shell 402 and the second wall portion 428*a* of the liner 406*a* can be substantially zero. For example, in various embodiments the angle $\alpha$ can be about zero degrees to about six degrees.

According to various embodiments, the second liner can be provided as a second liner 406*b* including a second exterior wall portion 428*b* to be positioned relative to the interior taper portion 414 of the shell 402. The second exterior wall portion 428*b* can be provided with a substantially non-complementary taper relative to the interior taper 414 of the shell 402. For example, the second exterior wall portion 428*b* can be provided substantially parallel to a central axis 406' (illustrated in FIG. 4C). Accordingly, an angle $\beta$ can be formed between the interior taper wall 414 and the exterior wall 428*b*. The angle $\beta$ can be about one degree to about fifteen degrees between the internal taper wall 414 and the second wall portion 428*b*. Thus, the second wall portion 428, 428*a*, 428*b* can be provided with any appropriate configuration relative to the shell 402.

Figure 5A:
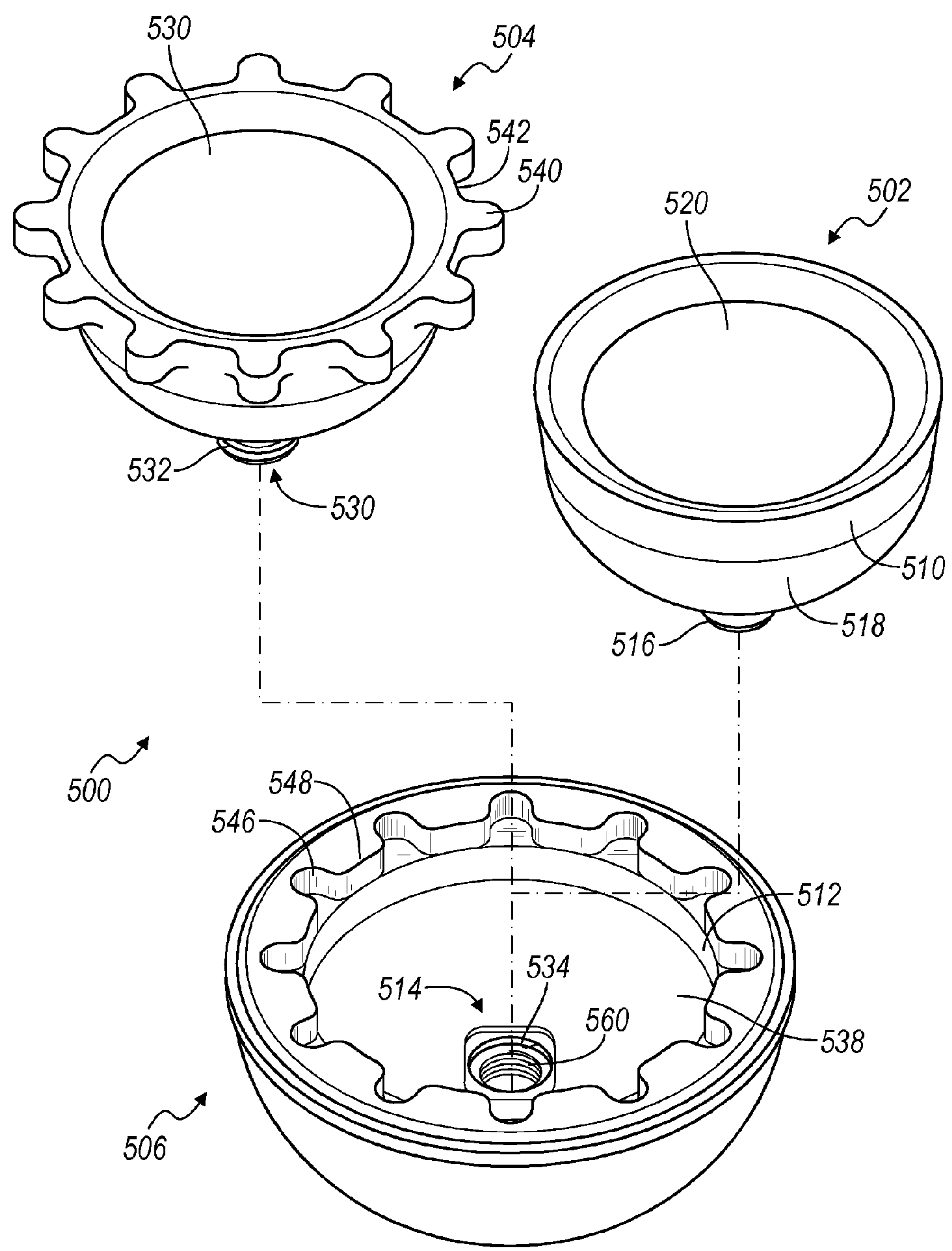
FIG. 5A is a perspective exploded view of an acetabular assembly, according to various embodiments.

According to various embodiments, an acetabular assembly 500 including first liner 502 and a second liner 504 that are both provided to be inserted or fixed to a single shell 506, is illustrated in FIG. 5A. The first liner 502 can be formed of any appropriate material, such as a rigid material, including a ceramic or other rigid materials, including those discussed above. The second liner 504 can be formed of a more flexible material, such as an ultra-high molecular weight polyethylene, or other appropriate materials, including those discussed above. Regardless, both the first liner 502 and the second liner 504 can be interconnected with the shell 506 in any appropriate manner, including those discussed further herein.

The first liner 502 can include an appropriate connection mechanism, such as a tapered wall, which can define a male taper 510. The male taper wall 510 can interconnect or connect with a female taper wall 512, defined by the shell 506. The interconnection of the two tapers, 510, 512, can include an appropriate taper connection, including those discussed above. For example, the two tapers, 510, 512 can be provided in an appropriate angle to provide a Morse taper fit between the first liner 502 and the shell 506. In addition, the shell 506 can include an apical depression or bore 514, which can engage or receive a projection or nipple 516 extending from an external wall 518 of the first liner 502. The projection 516 can enter the apical depression 514 to assist in aligning the first liner 502. The first liner 502 can also include an internal surface 520 for articulation with a selected portion, such as a femoral head implant or a natural femoral head.

The second liner 504 can also include an internal surface 530 that can articulate with any appropriate portion, such as a femoral head or a femoral implant. The second liner 504 can also include a projection or nipple 530 that can include a ring or extended portion 532 that can engage a locking depression or area 534 defined within the apical depression 514 of the shell 506. The shell 506 can define an interior surface 538 and the apical depression 514 allows the locking portion 534 to be positioned into a wall 539 of the shell 506 and outside of the interior surface or interior 538 of the shell 506. In addition, the second liner 504 can define an anti-rotation system including projections 540 and depressions 542 that can engage respective depressions 546 and projections 548 of the shell 506. Accordingly, the second liner 504 can resist rotation relative to the shell 506. The fixing system can be used to axially hold the second liner 504 within the shell 506.

Figure 5B:
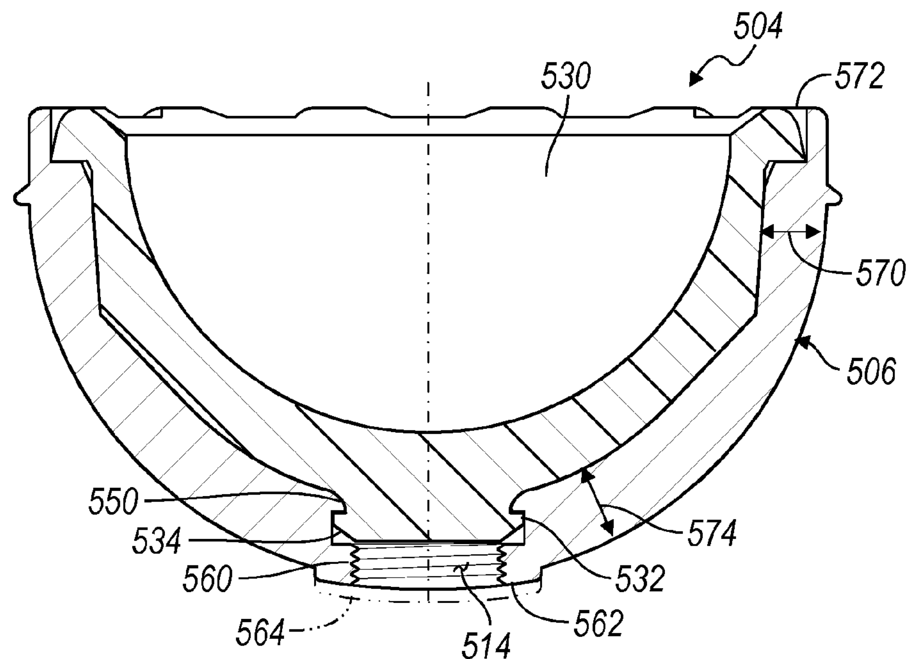
FIG. 5B is a cross-sectional view of a shell and liner connected, according to various embodiments.

As particularly illustrated in FIG. 5B, the second liner 504 can be positioned within the shell 506 so that the locking projection 532 is positioned within the locking depression 534 of the shell 506. The locking depression 534 of the shell 506 has a shell locking projection 550 that projects from a wall of the apical depression 514. The second liner 504 can be pressed into the shell 506 to allow the liner projection 532 to deflect as it passes over the shell projection 550 and then relax into the depression 534 to hold the second liner 504 relative to the shell 506.

The shell 506 can also define a thread 560 within the apical depression 514. The thread 560 can be defined in the apical depression 514 between the locking depression 534 and an exterior 562 of the shell 506. The shell 506 can define a bore in the apical depression 514 or it can include an optional thin wall 564 to cover or block the apical depression 514. The thin wall 564 can be provided for various purposes, such as eliminating or reducing particle migration out of the interior of the shell 506.

The wall of the shell 506 can include a first thickness 570 near a rim 572 of the shell 506 and a second thickness 574 near the apical depression 514. The second thickness 574 can be greater than the first thickness 570. The amount of the second thickness 574 can allow for the creation of the threads 560 near the apical depression 534 within the shell 506.

Figure 5C:
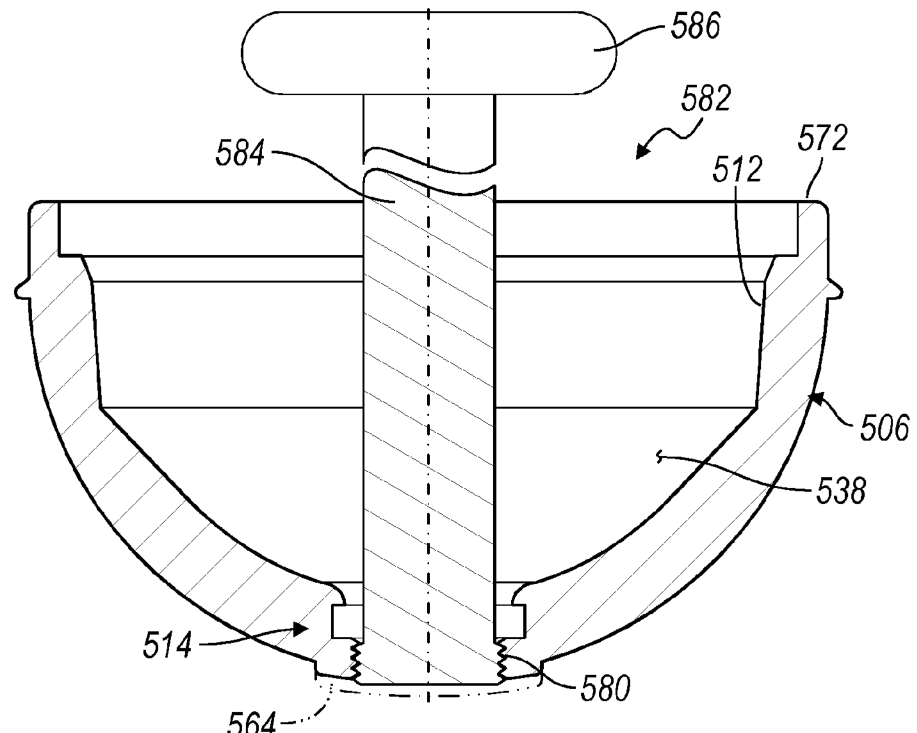
FIG. 5C is a cross-sectional view of a shell and insertion assembly according to various embodiments.

With continuing reference to FIG. 5B and additional reference to FIG. 5C, the threads 560 can be used to connect or interlock with complimentary threads 580 of an insertion instrument 582. The insertion instrument 582 can be any appropriate insertion instrument, such as the acetabular cup insertion instrument, sold by Biomet, Inc., having a place of business in Warsaw, Ind. The insertion instrument 582 can generally include a shaft 584 and an impaction head 586. It is generally understood the impaction tool 582 can readily engage the threads 560 of the shell 506 and an appropriate instrument, such as an impaction hammer, can contact the impaction head 586 to impact the shell 506 into the anatomy 1000 (FIG. 7). The threads 560 defined in the shell 506 can allow for a secure attachment of the impaction tool 586 to the shell 506 during implantation. After implantation, the impaction tool 582 can be efficiently unthreaded from the threads 560 defined by the shell 506 to remove the impaction tool 586 and allow inner connection of either the first liner 502 or the second liner 504.

Figure 6A:
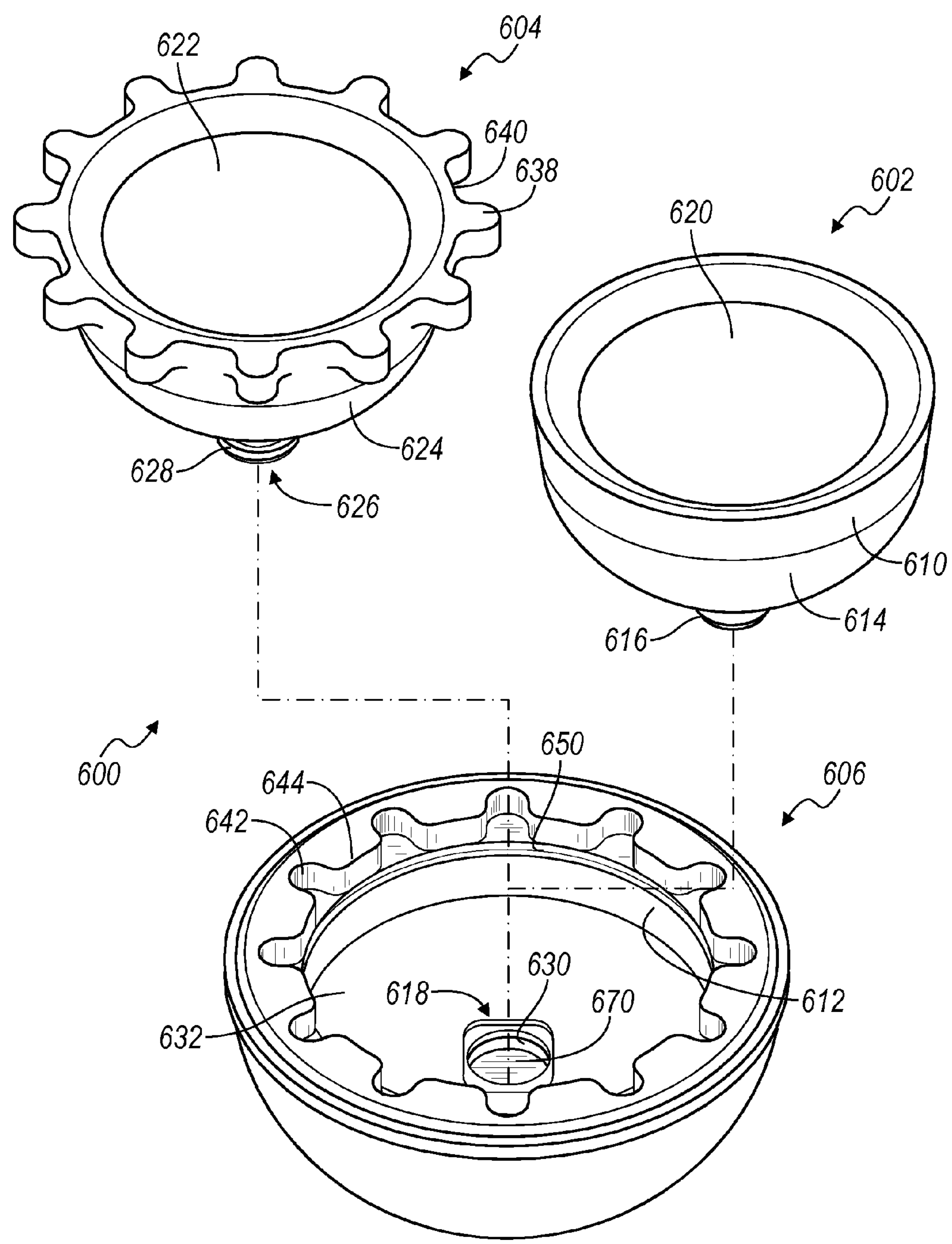
FIG. 6A is a perspective exploded view of an acetabular assembly, according to various embodiments.

According to various embodiments, an acetabular assembly 600 can include a first liner 602 and a second liner 604 that can both be provided to interconnect with a single shell 606, as illustrated in FIG. 6A. The first liner 602 can be a rigid liner, similar to the rigid liners discussed above. In addition, the second liner 604 can be a more supple or flexible liner, similar to those discussed above.

The first liner 602 can define a male taper wall 610 that can engage a female taper wall 612 in an appropriate manner, such as with a Morse taper locking connection or other appropriate connection as discussed above. The first liner 602 can also include an external wall 614 from which a nipple or aligning projection 616 can extend. The aligning projection 616 can engage or cooperate with an apical depression or bore 618 defined by a wall of the shell 606. As discussed above, the aligning projection 616 can be positioned within the apical depression 618 to assist in aligning the first liner 602 to allow for appropriate interconnection of the male taper 610 and the female taper 612. The first liner 602 can also include an interior surface 620 that can allow for articulation of an appropriate portion, such as a femoral head implant or a femoral head.

The second liner 604 can also include an interior surface 622 for articulation with a femoral head implant or a femoral head. The second liner 604 can also include an exterior surface 624 from which a locking or holding projection 626 can extend. The locking projection 626 can include a locking portion 628 that can engage a locking depression 630 defined within the apical depression 618. The shell 606 can define or include an interior that is defined by an interior wall 632. The apical depression 618 can allow for the locking depression 630 to be positioned outside of the interior or the interior wall 632 of the shell 606. The second liner 604 can also include an anti-rotation mechanism or a system including anti-rotation projections 638 and respective depressions 640. The projections and depressions 638, 640 of the second liner 604 can cooperate with respective depressions 642 and projections 644 of the shell 606 to allow for the second liner 604 to resist rotation relative to the shell 606. The locking portion 628 holds the second liner 604 axially relative to the shell 606.

Figure 6B:
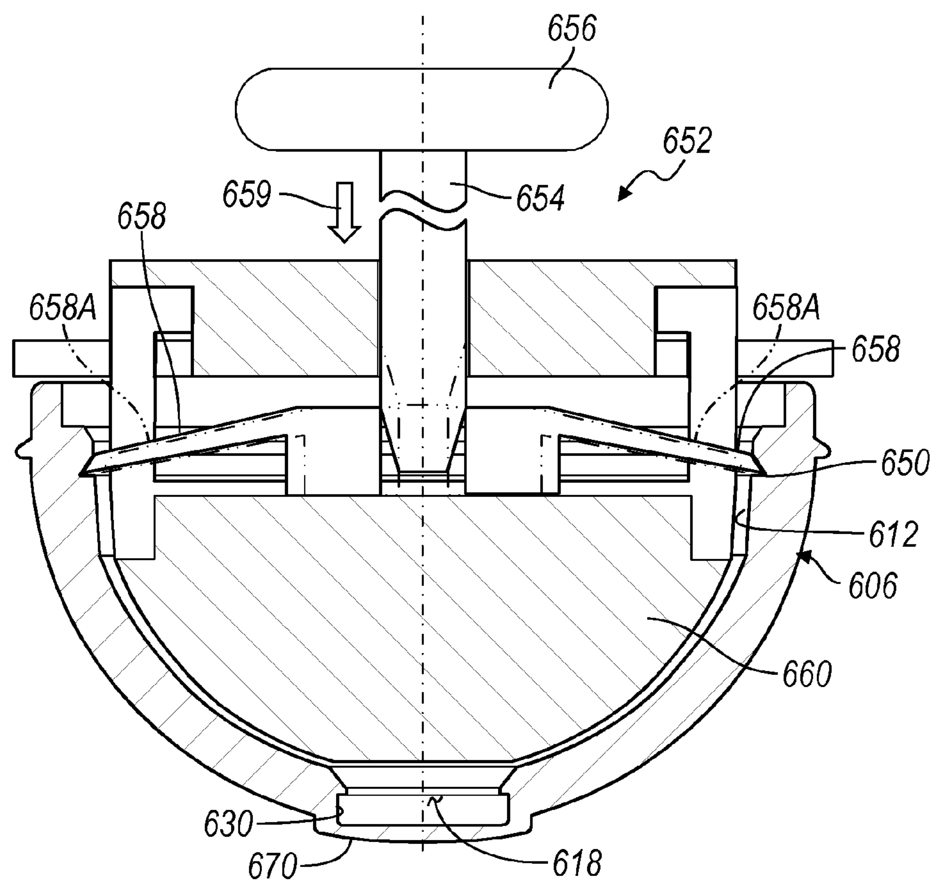
FIG. 6B is a cross-sectional view of a shell and a positioning instrument.

With continuing reference to FIG. 6A and additional reference to FIG. 6B, the shell 606 can also include or define an implantation depression 650. The implantation depression 650 can be an angular ring or depression defined within the inner wall 632 of the shell 606. In addition, the implantation depression 650 can be defined in an area that further defines the female taper 612. The implantation depression 650, however, can be provided to allow for engagement or cooperation with an implantation instrument 652. The implantation instrument can be any appropriate implantation instrument, such as the inserter instrument used with the Regenerex® revision cup system sold by Biomet, Inc., having a place of business in Warsaw, Ind. Briefly, the implantation or impaction instrument 652 could include a shaft 654 having an impaction head 656. The impaction instrument 652 is diagrammatically illustrated merely for exemplary purposes and may be augmented for particular implantation procedures or cups. Nevertheless, the impaction or implantation instrument 652 could include projecting or engaging arms 658 that can move from a retracted position 658*a*, (shown in phantom) to an extended position to engage the implantation Depression 650 as the impaction head 656 is moved in the direction of arrow 659 toward the apical depression 618. An interior wall engaging head 660 can also be provided to align the impaction instrument 652 and engage the interior surface 632 of the shell 606. Nevertheless, the arm 658 can engage the implantation depression 650 to allow for an appropriate implantation or impaction force to be provided to the shell 606 as it is implanted into the anatomy 1000 (FIG. 7).

A wall, such as a thin wall 670, can also be provided near the apical depression 618. The apical depression 618 can, therefore, be completely closed to an exterior of the shell 606. As discussed above, the thin wall can assist in eliminating or reducing particle migration out of the interior of the shell 606.

Figure 6C:
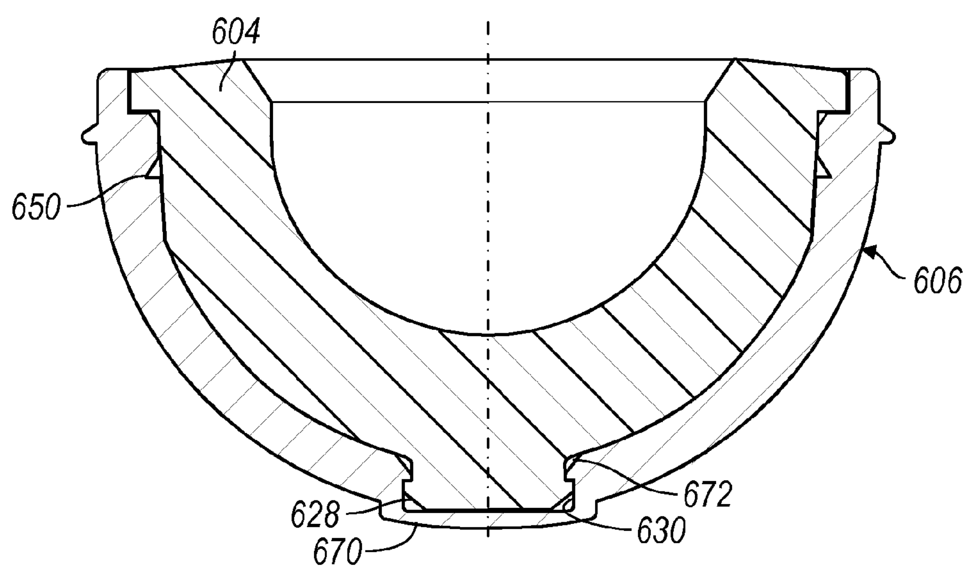
FIG. 6C is a cross-sectional view of a shell and the liner connected.

With additional reference to FIG. 6C, the second liner 604 can be positioned within the shell 606 by pressing the locking portion 628 past a shell locking projection 672 into the shell locking or receiving depression 630. As discussed above, the thin wall 670 can define an exterior to the apical depression 618 defined by the shell 606. The second liner 604 can be substantially held within the shell 606 with the interaction or cooperation of the receiving groove 630 defined by the shell 606 outside of the interior 632 and the holding projection 628 defined by the second liner 604. The implantation depression 650 does not engage or hold the second liner 604 within the shell 606. Additionally, the implantation depression 650 does not cooperate with the first liner 602 to hold the first liner 602 within the shell 606.

It will be understood that the acetabular assemblies, according to various embodiments, can be provided for use by a user such as a surgeon. In addition, the various assemblies can be altered for various purposes. For example, an acetabular assembly can include both the liner 306 and the liner 206 with the liners 304 and 204, which may be substantially similar. In addition, multiple shells may be provided including the characteristics of two or more shells 22, 202, 302, 302', 402, 506 and 606. Therefore, it will be understood that an assembly can be provided for any appropriate purpose.

Further, the various liners and shells can be formed of any selected or appropriate materials, as is understood by one skilled in the art. Therefore, although exemplary materials are provided for both a hard or rigid liner and a soft or flexible liner, other appropriate materials can be used.

An acetabular assembly, according to various embodiments including those discussed above, can be implanted relative to the acetabulum 18 of an anatomy 1000. With reference to FIG. 7, the anatomy 1000 can include a pelvis 1002 which can define the acetabulum 18. Physically interconnected with the pelvis 1002 can be a spinal column 1004 of a patient having the anatomy 1000. It will be understood that the acetabular assemblies illustrated above can be implanted in an appropriate manner. According to various embodiments, however, the acetabular assembly 20 can be implanted as discussed herein. It will be understood that the other acetabular assemblies can be implanted in a similar manner with variations for the specifics of the liners and shells discussed above. In addition, the liners, according to various embodiments, can include constraining liners, such as those that include high walls and other features.

Exemplary liners or implant systems include Ringloc® Liners sold by Biomet, Inc. of Warsaw, Ind., USA.

As illustrated in FIG. 7, the shell 22 can be positioned within the acetabulum 18 in any appropriate manner. One skilled in the art will understand that the acetabulum 18 can be prepared in any appropriate manner, for example via reaming, cement placement, or fastener placement. The shell 22 can be fixed to the acetabulum 18 in any appropriate manner. For example, a cementless fixation can be used, a cement fixation, a screw or member fixation or any other appropriate fixation. For example, Ringloc® acetabular cup systems can be implanted with cement, without cement, and with or without screws or other fixation members.

During an operative procedure, once the surgeon has positioned the shell 22 within the acetabulum or even prior to the positioning of the shell 22, but after the beginning of a procedure, a surgeon may determine that a different type of prosthesis may be necessary or that damage to the anatomy is greater based upon visual inspection as opposed to other types of inspection. Therefore, once the procedure has begun either the first liner 24, which can be a substantially hard or rigid liner, can be positioned within the shell 22 or the second liner 26, which can be a softer liner, can be positioned within the shell 22. The selection of either of the liners 24, 26 for positioning within the shell 22 can allow for other options in a procedure, such as positioning of a femoral head implant 32*a*, 32*b* or maintaining a natural femur head 34 for articulation. The head implant 32*a*, 32*b* can include various materials, such a metal, ceramic, or other appropriate materials. Also, the diameter or size of the implant 32*a*, 32*b* can depend on materials, patient size, etc. A kit of different sizes can be provided, if selected. It can also be selected to have the head implant 32*a*, 32*b* to be of the same material as the liner, according to various embodiments.

For example, during a preoperative planning stage, a surgeon may determine that a femoral implant 32 may be necessary and the surgeon may desire to use the first liner 24, which is substantially rigid. The surgeon may, however, desire to have an option of maintaining the natural femur 34, allowing it to articulate with the softer second liner 26. Therefore, the acetabular assembly 20 may be provided to allow the surgeon such an option. Once the procedure has begun, and based on visual inspection, the surgeon may determine that the femoral implant 32 is necessary and prepare the femur for the implantation of the implant 32, and select the first liner 24 for positioning into the shell 22. The surgeon may, alternatively, determine that the natural femoral head 34 is salvageable and elect to position the second liner 26 within the shell 22 for articulation with the natural femoral head 34. Therefore, the acetabular assembly 20 can allow for the connection of either the first liner 24 or the second liner 26 during an operative procedure.

Once the selection of the liner is made, the liner can be positioned within the shell 22. For example, if the first liner 24 is selected to be used, the interconnection of the male taper 44 of the first liner 24 and the female taper 40 of the shell 22 can be used to interconnect the first liner 24 with the shell 22. Alternatively, the connecting member 28 can be used to engage the connecting first groove 72 of the shell 22 if the second liner 26 is provided.

As discussed above, the provision of the two connection portions, the female/male taper connection or the connecting member connection in the respective grooves 72, 74, positions the different connecting portions at a distance from one another. Therefore, the first connecting system will not interfere with the second connecting system of the acetabular assembly 20.

In addition, it will be understood that any appropriate instruments can be used to insert either of the selected liners 24, 26 and further that the procedure for the implantation can proceed to any appropriate plan selected by a surgeon. The selection of the liners relative to a single shell, however, can allow for selectability during an operative procedure allowing for efficiency in the procedure and selection by the surgeon resulting in a selected outcome for the patient.

According to various embodiments of the acetabular assembly, the liners, such as the liners 24, 26 of the acetabular assembly 20, can each be connected with a connection portion (i.e. the taper connection 40, 44 or the connecting member 28 and grooves 72, 74). Each of the connection portions interconnecting the respective liners 24, 26 with the shell 22 can be engaged completely or substantially independently of the other depending upon the liner positioned within the shell 22. Therefore, when the female taper 40 is engaged with the male taper 44, the connecting member 28 need not engage the first groove 72 defined by the shell 22.

According to various other embodiments, such as the acetabular assemblies 200, 300, the various liners can separately and distinctly engage one of the two or more connecting portions or areas provided with the shell 202, 302. According to various embodiments, the first liner 204 can include the button 205 that engages the apical opening in the shell 202, but does not engage the apical opening 220 for holding the first liner 204 relative to the shell 202. Similarly, the first liner 304 can include the nipple 305 that can engage the apical opening 333 in the shell 302. The guide buttons 205, 305 can assist in guiding the liners 204, 304 into the shell 202, 302. This can assist in assuring an appropriate alignment of the taper connections between the liners 204, 304 and the shells 202, 302. In addition, the second liners 206, 306 can include complementary exterior shapes to engage, substantially flushly, the interior of the respective shells 202, 302 but do not engage the tapers in a fixed manner. As discussed above, the second liners 206, 306 can be formed of a material that is generally soft or flexible. Therefore, the tapers defined by the respective shells 202, 302 do not need to securely engage or fixedly engage the liners 206, 306 within the shells 202, 302. The second connecting portion defined within the apical hole of the shells 202, 302 holds the liners 206, 306 axially within the shells 202, 302.

In the alternative, however, the liners, according to various embodiments, can engage more than one connecting portion relative to the shell, according to various embodiments. For example, with reference to FIGS. 1B and 1C, the first liner 24 can include both the male taper 44 and a groove 74*a*, shown in phantom, to engage the connecting member 78, similar to the connection in FIG. 1C. In this way, the first liner 24 can engage the shell 22 at two positions. Similarly, as discussed above the second liner 26 can also include the button or projection 89 that can be positioned in or engage the female taper 42. Thus, the second liner 26 can also engage the shell 22 both with the locking member 78 and in the female taper 42.

Similarly, liners according to various embodiments can engage shells, according to various embodiments, at more than one connection location. As a further example, the first liner 204 can include both the male taper 272 and a button 205 that includes a groove 205*a* to engage the connection member 208. Similarly, the second liner 206 can include a male taper 207 that can engage or connect with the female taper 216 of the shell 202. Thus, liners of various embodiments can engage shells of various embodiments at two or more portions or locations to connect the liners to the shells.

The first connection portion and the second connection portion can be positioned, as discussed above, at selected distances from one another defined by a shell, such as the shell 22. As discussed herein, a first connection portion, including the female taper 40 can be positioned at an apex or proximal position (as defined by the implantation position of the shell 22). The second connection portion, including the first groove 72, is positioned substantially near or at the rim 70 or distal position of the shell 22.

Returning reference to FIG. 1 B, the first connection portion 72 is positioned at least above a plane or line A that can divide the shell 22 in half by height between the rim 70 and a an apex point. It will be understood that the position of the first groove 72 may be altered relative to the middle line A, but generally is positioned above the middle line relative to the shell 22. In addition, it will be understood that a similar line may be positioned substantially one third towards the rim 70 or towards the apex point 41 of the shell 22 where the female taper 40 is positioned below or towards the apex point 41 and the first groove 72 is positioned towards the rim 70, still substantially separated by the separating line A. It will be further understood that the various embodiments include similar positions of the first and second connection portions. A second line or plane A1 can define a proximal extent of the cavity or internal surface of the shell, according to various embodiments. The internal surface can extend from the rim to the line A1 to receive or engage a liner, according to various embodiments.

Therefore, the first and second connection portions, for example, including the female taper 40 and the first groove 72, can be positioned substantially separately and discreetly as defined by the shell 22, or any shell according to various embodiments. According to various embodiments, such as the shells 202 and 302, the female taper positioned substantially near the rims can be positioned with a similar separation line separating them from the second connection portion positioned near or at the apex or a proximal portion of the shells 202, 302. According to various embodiments, at least one connection portion can be positioned outside of the cavity, either beyond line A1 (such as within a wall of the shell) or beyond the rim of the shell.

As a further example, the shell 22 can define the internal surface 38 that extends from, at, or near the rim 70 to an apex internal surface, such as the part of the internal surface 38 that defies the thickness 54, 56. Thus, the first groove 72 can be positioned within the internal surface or cavity 38 of the shell 22. The apical opening defining the female taper 40, however, can be defined by the shell 22 having the thickness 54, 56. The shell wall 22*a* having the thickness 54, 56 can define the female taper 40 outside of the internal surface 38. In other words, the female taper 40 is defined between the internal surface 38 and an exterior surface 39 and not within a cavity or void defined by the internal surface 38.

According to various embodiments, one or both of the liners can engage both of the connection portions simultaneously or during or after implantation. Thus, one skilled in the art will understand that while discussion herein may be focused primarily upon connecting a liner with only one connection portion, that a liner can also be connected with two or more connection portions at the same time. The multiple connections can be provided for various reasons, such as securing the liner at more than one location, guiding the liner into an implantation position, reduction in manufacturing processes, etc.

According to various embodiments, an implant assembly for an anatomy includes a shell operable to be implanted into the anatomy, the shell including a first connection portion positioned at a first location relative to the shell and a second connection portion positioned at a second location remote from the first location. A first liner including a first liner connection portion operable to connectingly engage only the first connection portion of the shell and a second liner including a second liner connection portion operable to connect only to the second connection portion defined by the shell. The shell and the first liner and the second liner include complementary configurations such that the first connection portion is positionable near only the first liner connection and the second connection portion is positionable near only the second liner connection portion. Also, at least one of the first connection portions or the second connection portions defined by the shell can be defined within or by a wall of the shell such that it is not within a cavity or defined by an internal surface of the shell. The shell includes a wall that has an internal surface that defines a concave surface having an apex wherein the first connection portion is defined in the wall defining the concave surface. The first connection portion includes a taper wall defining a bore through the wall at or near the apex. The second connection portion includes a groove defined within the concave surface at or near the rim.

According to various embodiments, an implant assembly for positioning in an anatomy can include: a shell having a wall defining a distal rim and a proximal apex portion; a first connection portion defined by the shell near the distal rim; and a second connection portion defined by the wall of the shell near the proximal apex portion. The first connection portion and the second connection portion are separated completely by a transverse division line defined by the shell. A first liner defines a first liner distal rim and includes a first liner connection operable to engage the first connection portion near the first liner distal rim. A second liner defines a second liner proximal apex and includes a second liner connection operable to engage the second connection portion near the second liner proximal apex. The shell further includes an anti-rotation mechanism including at least one depression, functioning to receive a liner anti-rotation mechanism including at least one projection. The first liner defines the anti-rotation projection and further defines a groove forming at least a portion of the first liner connection, and further includes a connecting member operable to interconnect to the first connection portion and the first liner connection portion. The second liner defines at least a flexible finger forming at least a portion of the second liner connection wherein the second connection portion includes a depression from an internal surface defined by the shell to receive at least a portion of the finger. The first connection portion includes a taper or a groove and the second connection portion includes a taper, a groove, or a projection. The transverse division line is defined at least between a distal third of the shell and a proximal third of the shell. The first liner can be formed of a first material less rigid than a second material from which the second liner is formed. The first connection portion includes a groove defined by the shell and the first liner connection includes a groove defined by an exterior wall of the first liner, wherein a connecting member is operable to interconnect the first liner and the shell via interconnection with the first groove defined by the shell and the second groove defined by the first liner. The second liner defines a male taper which forms the second liner connection, and the second connection portion of the shell includes a female taper, wherein the interconnection of the male taper and the female taper locks the second liner to the shell. The shell includes a plurality of shells, wherein each of the plurality of the shells includes the second connection portion, each defining a female taper, wherein each female taper defined by each of the plurality of the shells includes a different height. The prosthesis can further include a femoral implant including a femoral head having a surface operable to move relative to at least one of the first liner or the second liner, wherein the shell is an acetabular shell operable to be implanted into an acetabulum of the anatomy.

According to various embodiments, a method of implanting a prosthesis assembly into an anatomy can include providing a first shell member, providing a first connection portion positioned at a first position relative to the shell, providing a second connection portion positioned at a second position relative to the shell, and providing the first position separated by a dividing line defined by the first shell from the second position. A first liner, including a first liner connection, operable to connect with only the first connection portion and a second liner, includes a second liner connection, operable to connect with only the second connection portion may also be provided. The method can further include selecting only one of the first liner or the second liner, and connecting the selected first liner or the second liner with the respective connection portion of the first shell member. The method can also include aligning the first or second liner relative to the shell member in order to align the respective first or second connection portion with the first liner connection or the second liner connection, wherein aligning includes at least positioning a positioning button within a bore defined by the first shell member. The method can further include implanting the first shell member into the anatomy, prior to connecting the selected first liner or the second liner with the respective connection portion. In addition, the method can include implanting the first shell member into the anatomy prior to selecting only one of the first liner or the second liner for connection to the first shell member. The method can also include beginning an operative procedure on the anatomy including visualizing a selected portion of the anatomy, and selecting only one of the first liner or the second liner based upon the visualization of the anatomy after the beginning of the operation. Positioning the first shell member in the anatomy after selecting only one of the first liner or the second liner, and connecting the first liner or the second liner to the first shell member after the first shell member has been positioned in the anatomy, may also be performed. Likewise, the method can include resecting a portion of the femur of the anatomy and implanting a femoral implant into the anatomy, wherein selecting only one of the first liner or the second liner includes selecting the first liner or the second liner to form an articulation with the femoral implant. An operating theater can be provided, where an operation is occurring, with at least the first shell member, the first liner, and the second liner; wherein selecting only the first liner or the second liner includes selecting only the first liner or the second liner for connection with the first shell member; and wherein selecting only the first liner or the second liner occurs during the operative procedure. In further detail, providing a first connection portion can include providing at least a depression in the first shell member and providing a groove in an interior wall of the depression provided in the first shell member; wherein the depression extends from a concave surface defined by the first shell member; wherein providing the first liner connection portion includes providing an extending portion extending from the first liner and a groove provided in the extending portion.

These teachings are merely exemplary in nature, thus, variations that do not depart from the gist thereof are intended to be within the scope of the teachings. Such variations are not to be regarded as a departure from the spirit and scope of these teachings.

What is claimed:

1. An acetabular implant assembly for positioning in an anatomy, comprising:

a shell with a shell wall extending from a proximal apex portion to a distal rim, the distal rim defining a first passage operable to receive a liner, wherein the shell has an internal wall surface defining an internal void and an external wall surface;

a first connection portion formed in the shell by the internal wall near the distal rim;

a second connection portion formed in a bore defined by a bore wall that extends through the shell wall from the internal wall surface to the external wall surface near the proximal apex portion;

a curved wall portion defined by the shell wall extending between the first connection portion and the second connection portion;

wherein the distal rim of the shell defines a rim plane and a central line extending substantially normal to the rim plane extends through the proximal apex portion;

wherein the first connection portion and the second connection portion are separated completely by a division line transverse to the central line defined in the shell;

a first liner having a first liner distal rim, a first liner proximal apex, a first liner connection portion formed by an exterior of the first liner configured to engage the first connection portion near the first liner distal rim, and an alignment nipple disposed at the first liner proximal apex that is aligned with and received by the bore extending through the shell wall, the alignment nipple having a smooth exterior such that the alignment nipple is not retained by the second connection portion formed in the bore; and a second liner defining a second liner distal rim, a second liner proximal apex, and a second liner connection portion configured to engage the second connection portion near the second liner proximal apex, wherein the second liner connection portion includes a locking nipple extending along a nipple axis from an outer surface of the second liner and an extending portion that extends substantially transverse to the nipple axis, wherein the extending portion is configured to pass, engage, and be retained by the second connection portion, and wherein the first liner is formed of a first material that is more rigid than a second material that forms the second liner.

2. The implant assembly of claim 1, wherein the first connection portion includes a taper and the second connection portion includes a groove;

wherein the first connection portion and the second connection portion are configured to be engaged without rotation.

3. The implant assembly of claim 1, wherein the division line is defined at least between a distal third of the shell and a proximal third of the shell.

4. The implant assembly of claim 1, further comprising:

a femoral implant including a femoral head having a surface operable to move relative to at least one of the first liner or the second liner.

5. The implant assembly of claim 1, wherein the extending portion includes a first wall that extends substantially perpendicular to the nipple axis and a second wall that is angled relative to the nipple axis.

6. The implant assembly of claim 5, wherein the second connection portion includes a ledge extending into the bore from the bore wall to engage the extending portion.

* * * * *